(12) United States Patent
Takagi

(10) Patent No.: US 9,379,521 B2
(45) Date of Patent: Jun. 28, 2016

(54) GROUP III NITRIDE SEMICONDUCTOR LASER DEVICE, METHOD FOR PRODUCING GROUP III NITRIDE SEMICONDUCTOR LASER DEVICE, METHOD FOR EVALUATING END FACET FOR OPTICAL CAVITY OF GROUP III NITRIDE SEMICONDUCTOR LASER DEVICE, AND METHOD FOR EVALUATING SCRIBE GROOVE

(71) Applicant: Sumitomo Electric Industries, Ltd., Osaka-shi (JP)

(72) Inventor: Shimpei Takagi, Osaka (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 14/435,977

(22) PCT Filed: Jul. 24, 2013

(86) PCT No.: PCT/JP2013/070050
§ 371 (c)(1),
(2) Date: Apr. 15, 2015

(87) PCT Pub. No.: WO2014/061328
PCT Pub. Date: Apr. 24, 2014

(65) Prior Publication Data
US 2015/0270686 A1    Sep. 24, 2015

(30) Foreign Application Priority Data

Oct. 16, 2012 (JP) ................................. 2012-228933

(51) Int. Cl.
*H01S 5/343* (2006.01)
*H01S 5/00* (2006.01)
(Continued)

(52) U.S. Cl.
CPC .......... *H01S 5/34333* (2013.01); *G01N 21/958* (2013.01); *H01S 5/0014* (2013.01);
(Continued)

(58) Field of Classification Search
CPC . H01S 5/34333; H01S 5/0425; H01S 5/0206; H01S 5/3202; H01S 5/0202; H01S 5/0014; H01S 5/028; H01S 5/32341
See application file for complete search history.

(56) References Cited

U.S. PATENT DOCUMENTS

| | | | | |
|---|---|---|---|---|
| 2011/0058585 | A1* | 3/2011 | Yoshizumi | B82Y 20/00 372/45.01 |
| 2012/0088326 | A1* | 4/2012 | Yoshizumi | B82Y 20/00 438/33 |
| 2012/0128016 | A1* | 5/2012 | Adachi | B82Y 20/00 372/43.01 |

FOREIGN PATENT DOCUMENTS

| | | |
|---|---|---|
| JP | 2009-081336 A | 4/2009 |
| JP | 4475357 | 3/2010 |

(Continued)

OTHER PUBLICATIONS

International Preliminary Report on Patentability in International Application No. PCT/JP2013/070050, dated Apr. 30, 2015.

(Continued)

*Primary Examiner* — Dung Nguyen
(74) *Attorney, Agent, or Firm* — Venable LLP; Michael A. Sartori

(57) ABSTRACT

A group III nitride semiconductor laser device comprises a laser structure including a support base of the group III nitride and first and second end facets for a laser cavity, and the first and second end facets intersect with an m-n plane defined by the m-axis of the group III nitride and an axis normal to a semipolar primary surface of the support base. A +c axis vector for a c-axis of the group III nitride forms an angle ALPHA in a range of 71 to 79 degrees with the normal axis. The +c axis vector is inclined at an angle $\alpha 1$ of 10 to 25 degrees with one normal vector defined at one edge of the first end facet, and is inclined at an angle $\beta 1$ of zero to 5 degrees with another normal vector defined at the other edge of the first end facet.

24 Claims, 18 Drawing Sheets

(51) Int. Cl.

| | | |
|---|---|---|
| *H01S 5/02* | (2006.01) | |
| *H01S 5/028* | (2006.01) | |
| *H01S 5/22* | (2006.01) | |
| *H01S 5/32* | (2006.01) | |
| *H01S 5/323* | (2006.01) | |
| *G01N 21/958* | (2006.01) | |
| *H01S 5/042* | (2006.01) | |

(52) U.S. Cl.
CPC ............ *H01S5/0202* (2013.01); *H01S 5/0206* (2013.01); *H01S 5/028* (2013.01); *H01S 5/0425* (2013.01); *H01S 5/2201* (2013.01); *H01S 5/3202* (2013.01); *H01S 5/32341* (2013.01)

(56) References Cited

FOREIGN PATENT DOCUMENTS

| | | |
|---|---|---|
| JP | 2011-003660 A | 1/2011 |
| JP | 2011-082459 A | 4/2011 |
| JP | 2011-135016 A | 7/2011 |
| JP | 2012-124273 A | 6/2012 |
| WO | WO-2011/077856 A1 | 6/2011 |
| WO | WO-2012/099221 A1 | 7/2012 |

OTHER PUBLICATIONS

International Search Report in PCT Application No. PCT/JP2013/070050 dated Oct. 22, 2013.

* cited by examiner

Fig.2
(a)
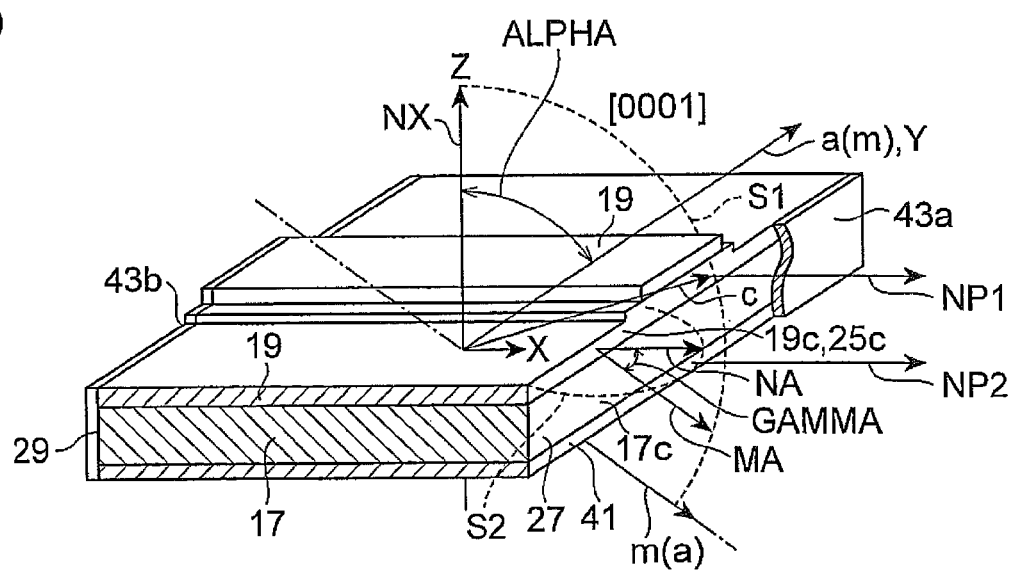
(b)
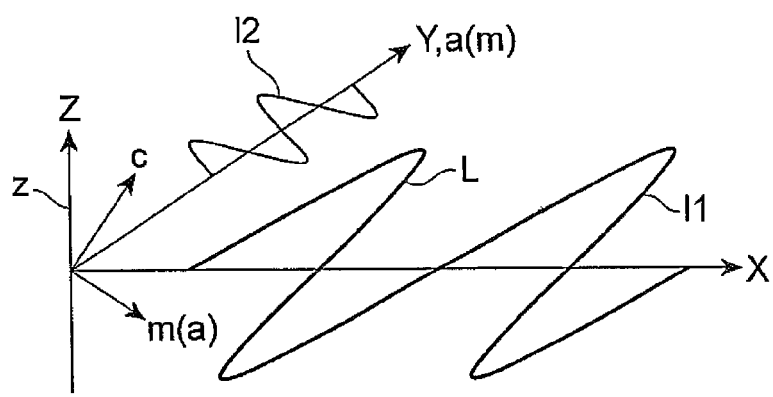

*Fig.7*
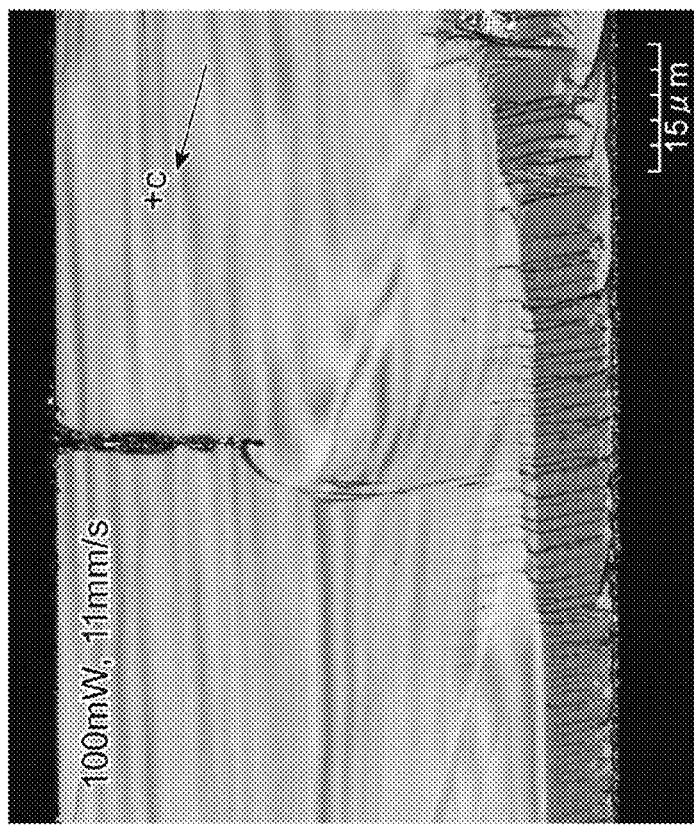
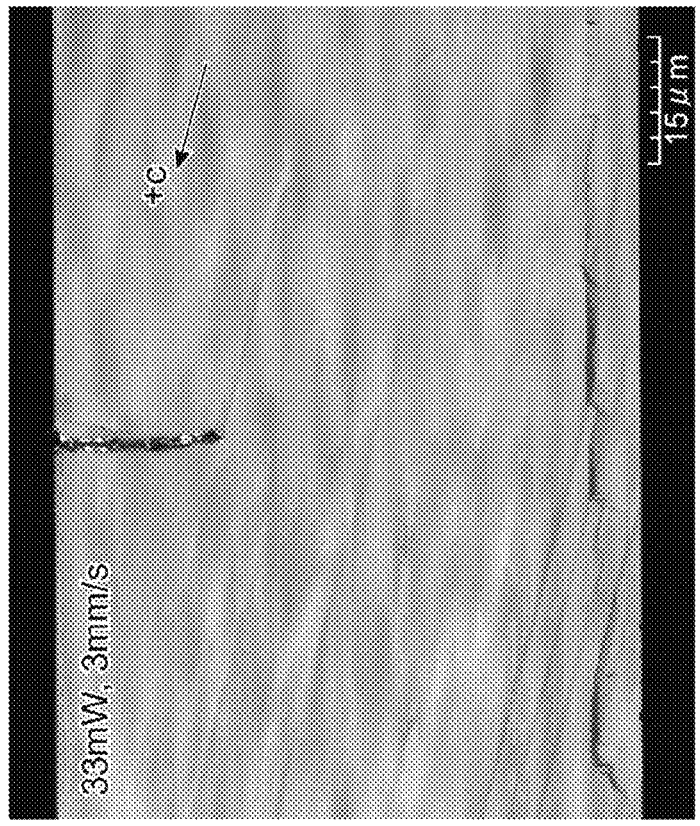

Fig.8
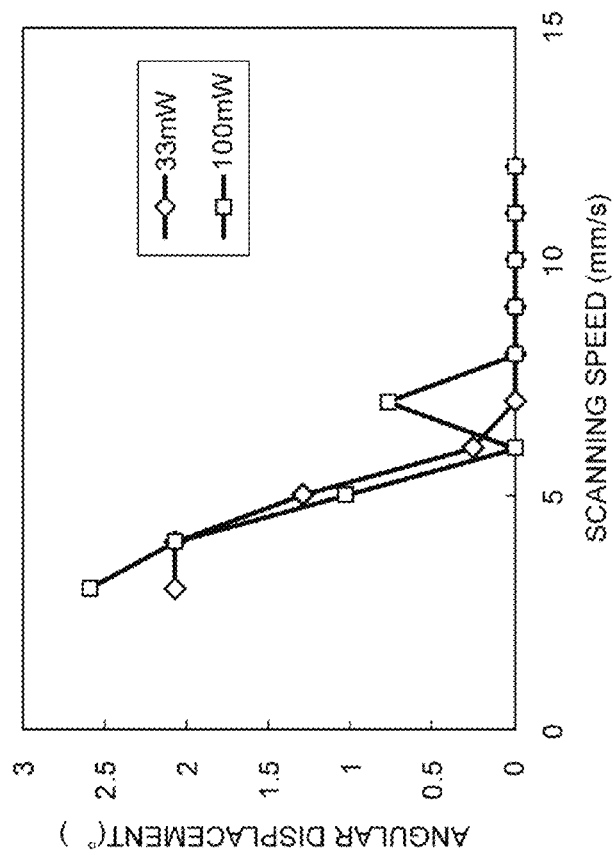
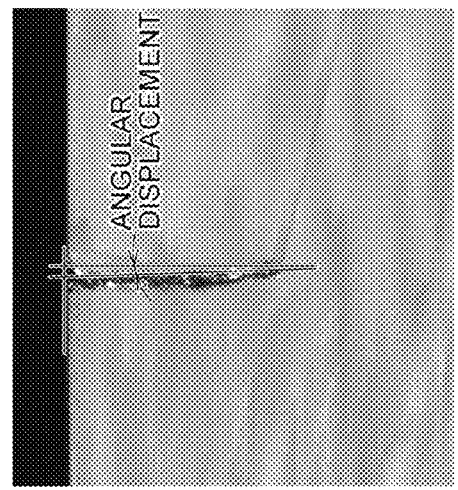

Fig.9
(a)
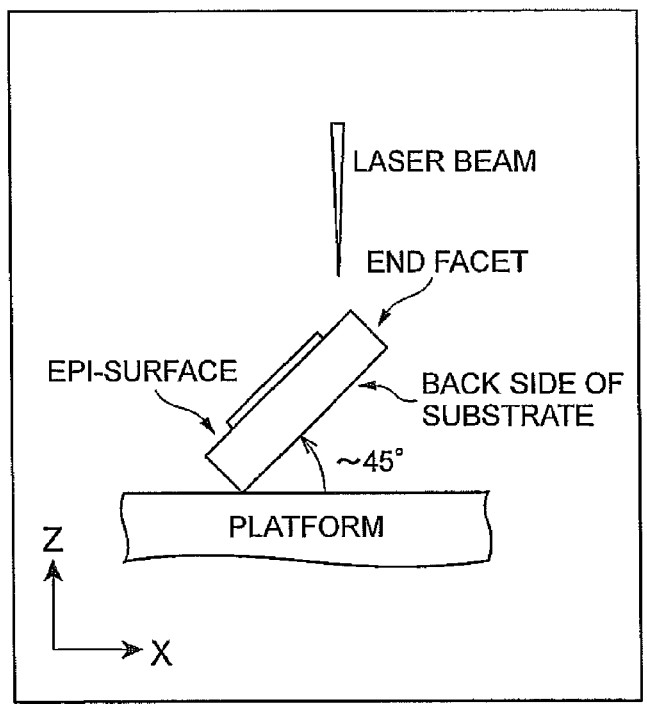
(b)
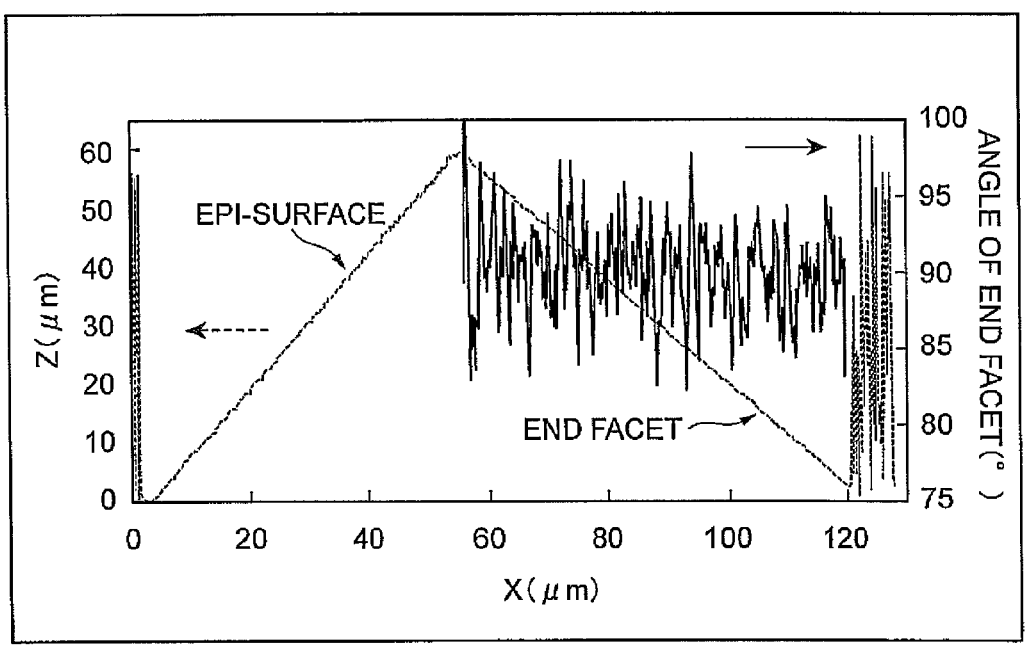

Fig.11
(a)
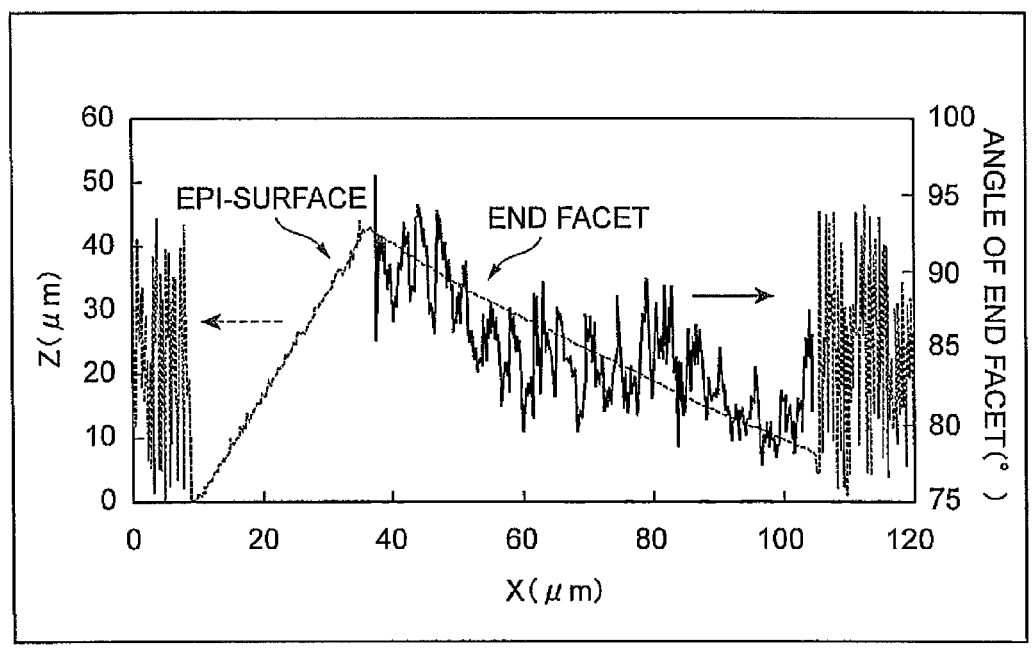
(b)
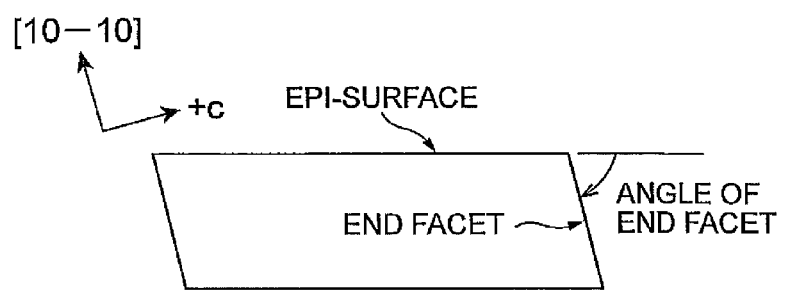

GROUP III NITRIDE SEMICONDUCTOR LASER DEVICE, METHOD FOR PRODUCING GROUP III NITRIDE SEMICONDUCTOR LASER DEVICE, METHOD FOR EVALUATING END FACET FOR OPTICAL CAVITY OF GROUP III NITRIDE SEMICONDUCTOR LASER DEVICE, AND METHOD FOR EVALUATING SCRIBE GROOVE

TECHNICAL FIELD

The present invention relates to a group III nitride semiconductor laser device, a method for producing the group III nitride semiconductor laser device, a method for evaluating an end facet for an optical cavity of the group III nitride semiconductor laser device, and a method for evaluating a scribe groove.

BACKGROUND ART

Patent Literature 1 discloses a nitride based semiconductor laser device that has a cleavage facet and a dry-etched surface. Patent Literature 2 and Patent Literature 3 each disclose a group III nitride semiconductor laser device formed on a semipolar surface.

CITATION LIST

Patent Literature

Patent Literature 1: Japanese Patent Application Publication No. 2009-081336
Patent Literature 2: Japanese Patent Application Publication No. 2011-003660
Patent Literature 3: Japanese Patent Application Publication No. 2011-135016

SUMMARY OF INVENTION

Technical Problem

The nitride based semiconductor laser device disclosed in Patent Literature 1 includes an n-type GaN substrate with a primary surface of a (11-22) plane, and a semiconductor laser device layer, which is formed on the (11-22) surface and includes an active layer. One of the ends of the semiconductor laser device layer is provided with an end facet for an optical cavity, and the end facet extends in a direction substantially perpendicular to the primary surface of the n-type GaN substrate. The n-type GaN substrate, on the other hand, has a device separation surface comprising a (0001) cleavage plane of the n-type GaN substrate, and this device separation surface is inclined at an angle of approximately 30 degrees with respect to the end facet for the cavity.

In the nitride based semiconductor laser device disclosed in Patent Literature 1, the end facet for the optical cavity has been formed by dry-etching, and then the n-type GaN substrate with the (0001) surface is cleaved to form a cleavage surface. Such process steps make the production of the nitride based semiconductor laser device complicated.

Patent Literature 2 discloses a group III nitride semiconductor laser device. This group III nitride semiconductor laser device has a laser cavity that demonstrates a low threshold current on a semipolar surface of a substrate in which the c-axis of the group III nitride is inclined toward the direction of the m-axis thereof. Patent Literature 3 discloses a group III nitride semiconductor laser device. This group III nitride semiconductor laser device uses a semipolar surface of a substrate in which the c-axis of the group III nitride is inclined toward the direction of the m-axis thereof, and angles at upper and lower edges of an end facet for the laser cavity are defined in the respective reference planes parallel to the semipolar surface of the substrate, and the end facet for the laser cavity is formed in such a manner that the above angles at the upper and lower edges become different from each other.

The knowledge provided by the inventors of the present invention is disclosed as follows: the surface aspect and quality of the end facet vary depending upon the orientation of the <0001> axis (or <000-1> axis) in the semiconductor device that uses the substrate with the semipolar surface in which the c-axis of the group III nitride is inclined toward the direction of the m-axis thereof; and the surface aspect and quality of the end facet can be controlled.

One aspect of the present invention is to provide a group III nitride semiconductor laser having a laser cavity, which is capable of reducing disturbance caused by return light, provided on a semipolar surface of a substrate in which a c-axis of the group-III nitride is inclined toward the direction of an m-axis thereof. Another aspect of the present invention is to provide a method for producing this group III nitride semiconductor laser. Yet another aspect of the present invention is to provide a method for producing a group III nitride semiconductor laser device, which can adjust the quality of an end facet allowing the emission, reflection, and/or transmission of a laser beam therethrough. Yet another aspect of the present invention is to provide a method for evaluating an end facet for an optical cavity of the group III nitride semiconductor laser device. An additional aspect of the present invention is to provide a method for evaluating a scribe groove for use in the formation of an end facet for the optical cavity of the group III nitride semiconductor laser device.

Solution to Problem

A group III nitride semiconductor laser device according to one aspect of the present invention comprises: (a) a laser structure including a support base and a semiconductor region, the support base being made of a hexagonal group III nitride semiconductor and having a semipolar primary surface, and the semiconductor region being provided on a semipolar primary surface of the support base; and (b) an electrode provided on the semiconductor region of the laser structure, a c-axis of the group III nitride semiconductor of the support base being oriented in a direction of a <0001> axis, the direction of the <0001> axis being indicated by a +c axis vector, the semiconductor region including an active layer, and the active layer including a gallium nitride based semiconductor layer, the c-axis of the group III nitride semiconductor of the support base forming an angle ALPHA with an axis normal to the semipolar primary surface in a direction away from the c-axis toward a [−1010] axis of the group III nitride semiconductor, the angle ALPHA being equal to or greater than 71 degrees but equal to or less than 79 degrees, the laser structure including a first end facet and a second end facet, the first end facet and the second end facet intersecting with an m-n plane defined by the normal axis and an m-axis of the group III nitride semiconductor, and a laser cavity of the group III nitride semiconductor laser device including the first end facet and the second end facet, the laser structure including a first surface and a second surface, the first surface being disposed on opposite side of the second surface, the semiconductor region being provided between the first surface and the support base, a first normal vector normal to the first end facet being defined at a first edge shared by the first end facet and the first surface, and the +c axis vector being inclined at an angle α1 with respect to the first normal vector within the m-n plane in a direction away from the [−1010] axis toward the c-axis, the angle α1 being equal to or greater than 10 degrees but equal to or less than 25 degrees, a second normal vector normal to the first end facet being defined at a second edge shared by the first end facet and the second surface, and the +c axis vector being inclined at an angle β1 with respect to the second normal vector within the m-n plane in the direction from the [−1010] axis toward the c-axis, the angle β1 being equal to or greater than zero degrees but equal to or less than 5 degrees, and an end facet of the support base and an end facet of the semiconductor region being exposed on each of the first end facet and the second end facet.

According to the above group III nitride semiconductor laser device, the angle α1 is different from the angle β1. In the first end facet near an epi-surface in the vicinity of the first surface, the angle that the first normal line and the c-axis form within the m-n plane is approximate to the angle α1 (e.g., an angle equal to or greater than 10 degrees and equal to or less than 25 degrees). This angular range can provide the first end facet in the vicinity of the first surface with an angle favorable to the optical cavity because of the angle ALPHA in a range of equal to or greater than 71 degrees and equal to or less than 79 degrees. Also, in the first end facet in the vicinity of the rear surface of the substrate, the angle that the second normal line and the c-axis form within the m-n plane is approximate to the angle β1 (e.g., an angle equal to or greater than 0 degrees but equal to or less than 5 degrees). This angular range enables the angle α1 and the angle β1 to have the same sign and enables the absolute value of the angle α1 to become greater than that of the angle β1. This results in that the first end facet in the vicinity of the second surface has an angle made greater than the angle favorable to the optical cavity. Reflection of light by the first end facet near the epi-surface and in the vicinity of the first surface (a part of the end facet around an end face of the active layer) can make a more significant contribution to lasing than the reflection of light created by the first end facet away from the first surface, and accordingly the component of light reflected by the part, far from the first surface, of the first end facet hardly acts as noise light.

A group III nitride semiconductor laser device according to one aspect of the present invention comprises: (a) a laser structure including a support base and a semiconductor region, the support base being made of a hexagonal group III nitride semiconductor and including a semipolar primary surface, and the semiconductor region being provided on the semipolar primary surface of the support base; and (b) an electrode provided on the semiconductor region of the laser structure, a c-axis of the group III nitride semiconductor of the support base being is oriented in a direction of a <0001> axis, the direction of the <0001> axis being indicated by as a +c axis vector, the semiconductor region including an active layer, and the active layer including a gallium nitride based semiconductor layer, the c-axis of the group III nitride semiconductor of the support base forming an angle ALPHA with an axis normal to the semipolar primary surface in a direction away from the c-axis toward a [−1010] axis of the group III nitride semiconductor, the angle ALPHA being equal to or greater than 71 degrees but equal to or less than 79 degrees, the laser structure including a first end facet and a second end facet, the first end facet and the second end facet intersecting with an m-n plane defined by the normal axis and an m-axis of the group III nitride semiconductor, and a laser cavity of the group III nitride semiconductor laser device including the first end facet and the second end facet, the laser structure including a first surface and a second surface, the first surface being disposed on opposite side of the second surface, the semiconductor region being positioned between the first surface and the support base, a first normal vector normal to the first end facet is defined at a first edge between the first end facet and the first surface, and the +c axis vector is inclined at an angle α1 with respect to the first normal vector within the m-n plane, in a direction away from the axis to the c-axis, a second normal vector normal to the first end facet being defined at a second edge shared by the first end facet and the second surface, and the +c axis vector being inclined at an angle β1 with respect to the second normal vector within the m-n plane in the direction from the [−1010] axis toward the c-axis, the angles α1 being different from the angle β1, the angles α1 and the angle β1 has the same sign, and an absolute value of the angle α1 being greater than that of the angle β1, the first end facet having a streak structure, the streak structure including streaks extending in a direction of an cross product of the c-axis and the m-axis, and each of the first end facet and the second end facet including an end facet of the support base and an end facet of the semiconductor region.

According to the above group III nitride semiconductor laser device, the angle α1 is different from the angle β1. In the first end facet near an epi-surface in the vicinity of the first surface, the angle formed by the first normal line with the c-axis within the m-n plane is approximate to the angle α1. Also, in the first end facet in the vicinity of the rear surface of the substrate, the angle formed by the second normal line with the c-axis within the m-n plane is approximate to the angle β1. When the angle ALPHA is equal to or greater than 71 degrees but equal to or less than 79 degrees, the angle α1 and the angle β1 have the same sign and the absolute value of the angle α1 is greater than that of the angle β1. Reflection of light in the first end facet near the epi-surface in the vicinity of the first surface (the end facet around the end face of the active layer) can make a more favorable contribution to the lasing than reflection of light by the first end facet away from the first surface, and the component of light reflected by the part, far from the first surface, of the first end facet hardly acts as noise light.

In the group III nitride semiconductor laser device according to an aspect of the present invention, the +c axis vector includes a normal component in a direction of the normal axis of the semipolar primary surface, and a parallel component in a direction parallel to the semipolar primary surface; the laser structure includes a laser waveguide structure extending on the semipolar primary surface of the support base; and the parallel component of the +c axis vector is in a direction from the second end facet toward the first end facet, and the laser waveguide structure extends in a direction of the parallel component of the +c axis vector.

In this group III nitride semiconductor laser device, when the parallel component of the +c axis vector points to the direction from the second end facet to the first end facet, in the first end facet, the angle that the end facet of the support base and the parallel component of the +c axis vector form can be made greater than the angle that the end facet of the epi-region and the parallel component of the +c axis vector form.

In the group III nitride semiconductor laser device according to an aspect of the present invention, the +c axis vector includes a normal component in a direction of the normal axis of the semipolar primary surface, and a parallel component in a direction parallel to the semipolar primary surface; the semiconductor region includes a first cladding layer made of a group III nitride semiconductor of a first conductivity type and a second cladding layer made of a group III nitride semiconductor of a second conductivity type, and the active layer is provided between the first cladding layer and the second cladding layer; the first cladding layer, the second cladding layer, and the active layer are epitaxially grown on the semipolar primary surface and arranged along a direction of the normal component of the +c axis vector; and the first cladding layer, the second cladding layer, and the active layer extend in a direction of the parallel component of the +c axis vector and compose a laser waveguide structure extending on the semipolar primary surface of the support base.

According to this group III nitride semiconductor laser device, the first cladding layer, the second cladding layer, and the active layer are epitaxially grown on the semipolar primary surface and arranged in the direction of the normal component of the +c axis vector VC, so that the crystal axis of the semiconductor region is associated with the crystal axis of the support base in direction. The formation of the end facets relates to the respective directions of +c axis vectors of the semiconductor region and the support. The breaking of the semiconductor region and the substrate propagates in association with the directions of the crystal axes.

In the group III nitride semiconductor laser device according to an aspect of the present invention, the −c axis of the group III nitride semiconductor of the support base extends in a direction opposite to a direction of a <000-1> axis; the direction of the <000-1> axis is represented as a c-axis vector; a third normal vector normal to the second end facet is defined at a third edge shared by the second end facet and the first surface, the c-axis vector is inclined at an angle α2 with respect to the third normal vector within the m-n plane in a direction away from the [−1010] axis toward the c-axis, and the angle α2 is +10 degrees to +25 degrees; a fourth normal vector normal to the second end facet is defined at a fourth edge shared by the second end facet and the second surface, the −c axis vector is inclined at an angle β2 with respect to the fourth normal vector within the m-n plane in the direction away from the [−1010] axis toward the −c axis, and the angle β2 is 0 degrees to +5 degrees, and the first end facet and the second end facet are provided to form in such a manner that the first end facet is configured as a light emission face.

According to this group III nitride semiconductor laser device, the angle α2 is different from the angle β2. In the second end facet near the epi-surface in the vicinity of the second surface, the angle that the third normal line and the c-axis form within the m-n plane is approximate to the angle β2 (e.g., an angle equal to or less than 0 degrees but equal to or greater than +5 degrees). This angular range provides the second end facet in the vicinity of the second surface with an angle favorable to reflecting light returning from the outside outward because the angle ALPHA is equal to or greater than 71 degrees but equal to or less than 79 degrees. This results in that reflection of light by the part of the second end facet located in the vicinity of the second surface and away from the epi-surface (a part of the end facet around the end face of the substrate) can contribute to the improvement of the stability of lasing.

In the group III nitride semiconductor laser device according to an aspect of the present invention, it is preferred that the support base have a thickness of 100 μm or less. According to this group III nitride semiconductor laser device, the substrate with this level of thickness can lead to a high yield in the formation of the first end facet with flatness and verticality which are appropriate for an optical cavity for the group III nitride semiconductor laser device.

In the group III nitride semiconductor laser device according to an aspect of the present invention, a laser beam from the active layer can be polarized in a direction of an a-axis of the group III nitride semiconductor. In this group III nitride semiconductor laser device, the band-to-band transition that can demonstrate the low threshold current has a polarization.

In the group III nitride semiconductor laser device according to an aspect of the present invention, light in an LED-mode of the group III nitride semiconductor laser device includes a polarization component I1 in a direction of the a-axis of the group III nitride semiconductor and a polarization component I2 in a direction of the projected c-axis of the group III nitride semiconductor onto the primary surface, and the polarization component I1 is larger than the polarization component I2. In this group III nitride semiconductor laser device, the laser cavity allows the LED-mode light with a high emission intensity to laser.

In the group III nitride semiconductor laser device according to an aspect of the present invention, it is preferred that the semipolar primary surface fall within a range of −4 degrees to +4 degrees with respect to a {20-21} plane. According to this group III nitride semiconductor laser device, a slight off-angle with respect to the typical semipolar surface can provide the first and second end facets with an equivalent flatness and verticality appropriate for a laser cavity of the group III nitride semiconductor laser device.

In the group III nitride semiconductor laser device according to an aspect of the present invention, it is preferred that the semipolar primary surface include a {20-21} plane. According to this group III nitride semiconductor laser device, this typical semipolar primary surface can demonstrate the first and second end facets with flatness and verticality sufficient to form a laser cavity of the group III nitride semiconductor laser device.

In the group III nitride semiconductor laser device according to an aspect of the present invention, it is preferred that the support base have a stacking fault density of $1\times10^4$ cm$^{-1}$ or lower. According to this group III nitride semiconductor laser device, the stacking fault density of $1\times10^4$ cm$^{-1}$ or lower is unlikely to fortuitously degrade the flatness and/or verticality of end facets for the optical cavity.

In the group III nitride semiconductor laser device according to an aspect of the present invention, the support base can be formed from GaN, AlGaN, AlN, InGaN, or InAlGaN. According to this group III nitride semiconductor laser device, the use of a substrate formed from any of these gallium nitride based semiconductors can obtain the first and second end facets that can be used as laser cavity. The use of an AlN substrate or an AlGaN substrate can increase the polarization degree and enhance the optical confinement effect due to their low refractive indices. The use of an InGaN substrate can reduce the ratio of lattice mismatch between the substrate and a light emitting layer, thereby improving the crystal quality thereof.

The group III nitride semiconductor laser device according to an aspect of the present invention can further comprises a dielectric multilayer film provided on at least one of the first end facet or the second end facet. End facet coating can also be applied to a fractured face of the group III nitride semiconductor laser device as well. The end facet coating can adjust the reflectivity of the end facet.

In the group III nitride semiconductor laser device according to an aspect of the present invention, the active layer includes a light emitting region generating light of a wavelength of equal to or greater than 360 nm but equal to or less than 600 nm. This group III nitride semiconductor laser device uses the semipolar surface, and the use of the semipolar surface can provide a group III nitride semiconductor laser device that allows effective use of polarization in the LED mode and demonstrates a low threshold current.

In the group III nitride semiconductor laser device according to an aspect of the present invention, the active layer includes a quantum well structure generating light of a wavelength of equal to or greater than 430 nm but equal to or less than 550 nm. In this group III nitride semiconductor laser device, the use of the semipolar surface allows the reduction in the piezoelectric field and the improvement of the crystal quality in the light emitting layer region, and hence improves the quantum efficiency, enabling generation of light with a wavelength of equal to or greater than 430 nm and equal to or less than 550 nm.

The group III nitride semiconductor laser device according to an aspect of the present invention can have a gain waveguide structure. The group III nitride semiconductor laser device can further comprise an insulating film provided on the semiconductor region, the electrode is in contact with the semiconductor region via an opening of the insulating film, and the angle α1 and the angle β1 are defined on an axis located at a center of a width of an opening of the insulating film and extending perpendicular to the semipolar primary surface of the support base, and the opening defines the gain waveguide structure. This group III nitride semiconductor laser device is applied to a semiconductor laser of a gain waveguide structure.

In the group III nitride semiconductor laser device according to an aspect of the present invention, the semiconductor region having the laser structure can have a ridge structure. The angle α1 and the angle β1 are defined on an axis located at a center of a width of an upper surface of the ridge structure, and the axis extends perpendicular to the semipolar primary surface of the support base. This group III nitride semiconductor laser device is applied to a semiconductor laser of a ridge structure.

In the group III nitride semiconductor laser device according to an aspect of the present invention, the first end facet and the second end facet extend from the first edge of the first surface to the second edge of the second surface; and an angle formed by an end facet of the active layer of the semiconductor region with a reference plane perpendicular to an m-axis of a support base of the nitride semiconductor is equal to or greater than −5 degrees but equal to or less than +5 degrees in a second plane, and the second plane is perpendicular to the normal axis and a first plane defined by the c-axis and m-axis of the group III nitride semiconductor.

This group III nitride semiconductor laser device not only has the end facet satisfying a desired verticality of the end facet in the angle within a plane defined the c-axis and the m-axis, but also satisfying the verticality of the end facet in the angle defined in the plane that is perpendicular to the normal axis of the semipolar surface.

A method for producing a group III nitride semiconductor laser device according to another aspect of the present invention has the steps of: (a) preparing a substrate made of a hexagonal group III nitride semiconductor and including a semipolar primary surface; (b) forming a substrate product including a laser structure and an electrode, the laser structure including the substrate and a semiconductor region formed on the semipolar primary surface; and (c) breaking the substrate product, a c-axis of the group III nitride semiconductor of the substrate extending in a direction of a <0001> axis, the direction of the <0001> axis being represented as a +c axis vector, in breaking the substrate product, scribing a first surface of the substrate product and then pressing a second surface of the substrate product to form a laser bar and another substrate product, the laser bar having an angle α1 and an angle β1, the angle α1 being equal to or greater than 10 degrees but equal to or less than 25 degrees and, the angle β1 being equal to or greater than zero degrees but equal to or less than 5 degrees, the scribing being executed in a direction intersecting with the +c axis vector, the laser bar having a first surface and a second surface, the first surface being provided on opposite side of the second surface, the laser bar having a first end facet and a second end facet, and each of the first end facet and the second end facet extending from the first surface to the second surface and being formed in a step of breaking the substrate product, the first end facet and the second end facet forming a laser cavity of the group III nitride semiconductor laser device, the first end facet and the second end facet intersect with an m-n plane defined by an m-axis of the group III nitride semiconductor and a normal axis normal to the semipolar primary surface, a first normal vector of the first end facet is defined at a first edge shared by the first end facet and the first surface, and the +c axis vector being inclined at the angle α 1 with respect to the first normal vector within the m-n plane in a direction away from a [−1010] axis of the group III nitride semiconductor toward the c-axis, a second normal vector of the first end facet being defined at a second edge shared the first end facet and the second surface, and the +c axis vector is inclined at the angle β1 with respect to the second normal vector within the m-n plane in the direction from the [−1010] axis to the c-axis, the semiconductor region including an active layer having a gallium nitride based semiconductor layer, the semiconductor region being provided between the first surface and the substrate, the c-axis of the group III nitride semiconductor of the substrate forming a nonzero angle ALPHA with the normal axis in the direction of the [−1010] axis of the group III nitride semiconductor, the angle ALPHA being equal to or greater than 71 degrees but equal to or less than 79 degrees, and the electrode being formed on the laser structure.

According to the method for producing a group III nitride semiconductor laser device, the angle α1 is different from the angle β1. In the first end facet near an epi-surface in the vicinity of the first surface, the angle formed by the first normal line and the c-axis within the m-n plane is approximate to the angle α1 (e.g., an angle equal to or greater than 10 degrees but equal to or less than 25 degrees). This angular range provides the first end facet in the vicinity of the first surface with an angle favorable to the optical cavity because the angle ALPHA is equal to or greater than 71 degrees but equal to or less than 79 degrees. Also, in the first end facet in the vicinity of the rear surface of the substrate, the angle formed by the second normal line and the c-axis within the m-n plane is approximate to the angle β1 (e.g., an angle equal to or greater than 0 degrees but equal to or less than 5 degrees). Since the angle α1 and the angle β1 have the same sign and the angle α1 is greater than the angle β1 because of the angle ALPHA that is equal to or greater than 71 degrees and equal to or less than 79 degrees, the first end facet in the vicinity of the second surface can be provided with an angle greater than angles demonstrating the optical cavity. Thus, reflection of light by the first end facet near the epi-surface in the vicinity of the first surface (a part of the end facet around an end face of the active layer) can make a more significant contribution to lasing than reflection of light in the first end facet away from the first surface, and the component of light reflected by the part, far from the first surface, of the first end facet hardly acts as noise light.

In the method for producing a group III nitride semiconductor laser device according to another aspect of the present invention, it is preferred that the scribing be executed using a laser scriber, the scribing produce a scribe groove, and that the scribe groove be shorter than the line of intersection of the first surface and an a-n plane defined by the normal axis and an a-axis of the group III nitride semiconductor.

According to this production method, breaking the substrate product results in forming another substrate product and a laser bar. This breaking of the substrate product is caused using a scribe groove that is shorter than a line to be separated for forming the laser bar.

In the method for producing a group III nitride semiconductor laser device according to another aspect of the present invention, the scribing can produce a scribe groove; the scribe groove extends from a front surface of the semiconductor region to the substrate; the scribe groove has an opening in the front surface of the semiconductor region and a bottom portion in the substrate; and a reference plane is defined by an edge of the opening of the scribe groove and an edge of the bottom portion of the scribe groove and extends in a direction of an a-n plane defined by the normal axis and an a-axis of the group III nitride semiconductor.

According to this producing method, it is preferred that the reference plane defined by the end of the opening of the scribe groove and the end of the bottom portion of the scribe groove be substantially parallel to the a-n plane. The inclination of the c-axis may cause the scribe groove to extend in the depth direction so as to be curved with respect to the primary surface of the substrate, but reducing the curve of the scribe groove contributes to obtaining the desired shape of an end facet as defined.

In the method for producing a group III nitride semiconductor laser device according to another aspect of the present invention, in the step of forming the substrate product, the substrate is processed by polishing to a thickness of 100 μm or less, and the second surface is a processed surface formed by the processing or a plane including an electrode formed on the processed surface.

According to this production method, the substrate with this level of thickness can lead to a high-yield formation of the first and second end facets having flatness and verticality sufficient for a laser cavity of the group III nitride semiconductor laser device.

In the method for producing a group III nitride semiconductor laser device according to yet another aspect of the present invention, it is preferred that the semipolar plane include a {20-21} plane. This production method allows the group III nitride semiconductor laser device to use the above typical semipolar surface, and can provide first and second end facets with flatness and verticality sufficient for the laser cavity.

In the method for producing a group III nitride semiconductor laser device according to yet another aspect of the present invention, the substrate comprises one of GaN, AlGaN, AlN, InGaN and InAlGaN. This production method allows the use of a substrate comprising any of these gallium nitride based semiconductors to form the first and second end facets that can be used as optical cavities.

The method for producing a group III nitride semiconductor laser device according to yet another aspect of the present invention has the steps of: (a) preparing one or plural articles, each article having a first surface and a second surface opposite to the first surface, and comprising a hexagonal group III nitride semiconductor crystal; (b) forming a first processed end facet in each article by carrying out a processing of the articles under respective processing conditions used for forming an end facet for an optical cavity of the group III nitride semiconductor laser device, the first surface having an edge shared with the first processed end face; (c) providing an evaluation of the first processed end facet by relatively scanning the first surface and the first processed end facet with a laser beam across the edge in an axial direction from one of the first surface or the first processed end facet to the other; (d) determining a processing condition based on the plural processing conditions by use of results of the evaluation; (e) preparing a substrate with a primary surface of a group III nitride semiconductor; (f) preparing a substrate product with a semiconductor region, the substrate, and an electrode, the semiconductor region being grown on the primary surface of the substrate; and (g) carrying out a processing of the substrate product under the determined processing condition to produce another substrate product and a laser bar from the substrate product, the laser bar having a first end facet and a second end facet, and the first end facet and the second end facet being formed through the processing of the substrate product, a laser cavity of the group III nitride semiconductor laser device having the first end facet and the second end facet, the hexagonal group III nitride semiconductor crystal being exposed on the processed end facet, the step of providing an evaluation of the first processed end facet deriving an angle of the processed end facet based on a result of the scanning of laser beam, the angle of the processed end facet being defined in the axial direction, and the angle of the processed end facet being defined as an angle formed by the first processed end facet with a reference plane extending along the first surface.

In this method for producing a group III nitride semiconductor laser device, the process for forming the end facet for the optical cavity is performed to the plural articles (e.g., samples) under the respective processing conditions, to form the first processed end facet in each article, and then the first surface and the first processed end facet are relatively scanned with a laser beam in a manner described above to evaluate the first processed end facet. This evaluation can measure the changing angle formed by the first processed end facet with the first surface (i.e., the verticality of the first processed end facet) through the profile of the reflected component of the laser beam. The evaluation result allows a desired processing condition to be found based on the plural processing conditions. With this desired processing condition, the process for forming the end facet for the optical cavity is performed to fabricate another substrate product and a laser bar from the aforementioned substrate product. This production method can provide a method for forming an end facet for an optical cavity, which can demonstrate the character distribution located at a quality close to a desired quality.

In the method for manufacturing a group III nitride semiconductor laser device according to yet another aspect of the present invention, the step of forming a first processed end facet includes the steps of: scribing the first surfaces of the articles under respective scribing conditions; and after scribing the first surface of the article, separating each article by pressing the second surface of the article to form a first fractured face, the first fractured face extending from the first surface to the second surface of the article, the step of forming another substrate product and a laser bar includes the steps of scribing a first surface of the substrate product using the determined scribing condition; and pressing a second surface of the substrate product so as to cause a separation of the substrate product, to form the another substrate product and the laser bar, the step of providing an evaluation of the first processed end facet includes a step of evaluating the first fractured face for the first processed end facet, the laser bar has a first surface and a second surface, the first surface being located on opposite side of the second surface, the first end facet and the second end facet extend from the first surface to the second surface of the laser bar, and the semiconductor region is provided between the first surface and the substrate.

According to this method for producing a group III nitride semiconductor laser device, the respective articles (e.g., a sample) are subjected to the process for forming an end facet for an optical cavity under plural processing conditions to form the first processed end facet in each article, and then the first surface and the first processed end facet are relatively scanned with a laser beam to evaluate the first processed end facet. This evaluation can provide information on the inclination angle formed by the first processed end facet with the first surface (i.e., the verticality of the first processed end facet) through the scanning of the laser beam. The evaluation result allows a desired processing condition to be found on the basis of the plural processing conditions. With this desired processing condition, the substrate product is subjected to the process to produce another substrate product and a laser bar from the aforementioned substrate product. This production method can provide a fabricating method, which can demonstrate the distribution of characteristics located at a quality close to a desired quality.

In the method for producing a group III nitride semiconductor laser device according to yet another aspect of the present invention, the scanning of laser beam can be performed using a laser microscope. According to this production method, the laser microscope facilitates the evaluation on the end facets. In the method for producing a group III nitride semiconductor laser device according to the present invention, the scribing can be performed using a laser scriber. According to this production method, using the laser scriber makes the control of the scribing easy.

In the method for producing a group III nitride semiconductor laser device according to yet another aspect of the present invention, the scribing conditions can include a scanning speed of the laser scriber. According to this production method, adjusting the scanning speed is advantageous to controlling the scribing associated with the present condition.

In the method for producing a group III nitride semiconductor laser device according to yet another aspect of the present invention, the primary surface of the substrate can be inclined with respect to a reference plane perpendicular to the c-axis of the group III nitride semiconductor of the substrate. This production method is used to make a device in which the primary surface of the substrate is inclined with respect to the reference plane perpendicular to the c-axis of the group III nitride semiconductor of the substrate.

In the method for producing a group III nitride semiconductor laser device according to yet another aspect of the present invention, the primary surface of the substrate can be inclined with respect to a reference plane perpendicular to an a-axis of the group III nitride semiconductor of the substrate. This production method is used to make a device in which the primary surface of the substrate is inclined with respect to the reference plane perpendicular to the a-axis of the group III nitride semiconductor of the substrate.

In the method for producing a group III nitride semiconductor laser device according to yet another aspect of the present invention, the primary surface of the substrate can be inclined with respect to a reference plane perpendicular to an m-axis of the group III nitride semiconductor of the substrate. This production method is used to make a device in which when the primary surface of the substrate is inclined with respect to the reference plane perpendicular to the m-axis of the group III nitride semiconductor of the substrate.

In the method for producing a group III nitride semiconductor laser device according to yet another aspect of the present invention, the substrate is made of a group III nitride semiconductor and includes a semipolar primary surface; a c-axis of the group III nitride semiconductor of the substrate is oriented in a direction of a <0001> axis; the direction of the <0001> axis is indicated by a +c axis vector; the substrate product has a laser structure, and anode and cathode electrodes provided on the laser structure; the +c axis vector includes a normal component in a direction of a normal axis normal to the semipolar primary surface, and a parallel component in a direction parallel to the semipolar primary surface; the semiconductor region includes a first cladding layer of a group III nitride semiconductor of a first conductivity type, an active layer, and a second cladding layer of a group III nitride semiconductor of a second conductivity type, and the active layer is provided between the first cladding layer and the second cladding layer; the first cladding layer, the second cladding layer, and the active layer are epitaxially grown on the semipolar primary surface and arranged along a direction of the normal component of the +c axis vector; and the first cladding layer, the second cladding layer, and the active layer extend in a direction of the parallel component of the +c axis vector and form a laser waveguide structure extending on the semipolar primary surface of the substrate.

According to this production method, the first cladding layer, the second cladding layer, and the active layer are epitaxially grown on the semipolar primary surface and arranged in the direction of the normal component of the +c axis vector. Accordingly, the crystal axis of the semiconductor region is associated with the crystal axis of the support base. The breaking of the semiconductor region and substrate propagates in association with the directions of the crystal axes.

In the method for producing a group III nitride semiconductor laser device according to yet another aspect of the present invention, the c-axis of the group III nitride semiconductor of the substrate is inclined away from the normal axis of the primary surface of the substrate toward a direction of the m-axis of the group III nitride semiconductor, and the first and second end facets intersect with an m-n plane defined by the normal axis and the m-axis of the group III nitride semiconductor. This production method is applicable to an embodiment in which the c-axis of the group III nitride semiconductor of the substrate is inclined toward the normal axis in the direction of the maxis of the group III nitride semiconductor.

In the method for producing a group III nitride semiconductor laser device according to yet another aspect of the present invention, the c-axis of the group III nitride semiconductor of the substrate can be inclined at an angle ALPHA with the normal axis of the primary surface therefrom in a direction from the c-axis to a [−1010] axis of the group III nitride semiconductor, the angle ALPHA being equal to or greater than 71 degrees but equal to or less than 79 degrees. This production method is applicable to an embodiment in which the c-axis of the group III nitride semiconductor of the substrate is inclined at the angle ALPHA with respect to the normal axis of the primary surface in the direction away from the c-axis of the group III nitride semiconductor of the substrate toward the [−1010] axis of the group III nitride semiconductor.

In the method for producing a group III nitride semiconductor laser device according to yet another aspect of the present invention, the semipolar primary surface can fall within a range of −4 degrees to +4 degrees from a {20-21} plane thereof. In this production method, a slight off angle with respect to the typical semipolar surfaces can provide the first and second end facets with flatness and verticality acceptable for a laser cavity of the group III nitride semiconductor laser device.

In the method for producing a group III nitride semiconductor laser device according to yet another aspect of the present invention, the c-axis of the group III nitride semiconductor of the substrate is inclined away from the normal axis of the primary surface of the substrate toward a direction of an a-axis of the group III nitride semiconductor, and the first and second end facets intersect with an a-n plane defined by the normal axis and the a-axis of the group III nitride semiconductor. This production method is applicable to an embodiment in which the c-axis of the group III nitride semiconductor of the substrate is inclined at an angle, greater than 0 degrees, away from the normal axis toward the direction of the a-axis of the group III nitride semiconductor.

In the method for producing a group III nitride semiconductor laser device according to yet another aspect of the present invention, the primary surface of the substrate can extend along a reference plane parallel to an orientation of any of a c-plane, an a-plane, and an m-plane of the group III nitride semiconductor of the substrate. This production method is applicable to an embodiment in which the primary surface of the substrate extends along a reference plane parallel to a plane orientation of any of a c-plane, an a-plane, and an m-plane of the group III nitride semiconductor of the substrate.

In the method for producing a group III nitride semiconductor laser device according to yet another aspect of the present invention, the article includes a group III nitride semiconductor substrate, and the group-III nitride substrate has a thickness of 400 µm or less. This production method can provide an evaluation on the relationship between the structure of the laser structure and the quality of the end facets, along with the end facet processing conditions for the end facets.

A method for evaluating an end facet for an optical cavity of a group III nitride semiconductor laser device according to yet another aspect of the present invention has the steps of: (a) preparing an object including a first surface, a second surface on opposite side of the first surface, and comprising a hexagonal group III nitride semiconductor crystal; and (b) scanning the first surface and an processed end facet with a laser beam in an axial direction from either the first surface or processed end facet of the object to the other across the edge therebetween, to evaluate the processed end facet using the laser beam scanning. The processed end facet of the object is formed under a processing condition for an optical cavity of the group III nitride semiconductor laser device, and extends along a plane intersecting with the first surface and the second surface, the group III nitride semiconductor crystal is exposed on the processed end facet, the step of evaluating the processed end facet obtains an angle of the processed end facet defined along the axial direction, from the result of the laser beam scanning, and the angle of the processed end facet is defined as an angle formed by the processed end facet with a reference plane extending along the first surface. This production method can evaluate the processed end facet in association with the structure of the processing condition and/or objects to be evaluated.

The method for evaluating an end facet for an optical cavity of a group III nitride semiconductor laser device according to yet another aspect of the present invention has the steps of: (a) preparing an object including a hexagonal group III nitride semiconductor crystal, the object having a first surface and a second surface provided on opposite side of the first surface and; (b) executing a processing of the object under a certain processing condition, to form a first processed end facet extending from an edge of the first surface, the processing being performed for forming an end facet for an optical cavity of the group III nitride semiconductor laser device; and (c) relatively scanning the first surface and the first processed end facet with a laser beam in an axial direction from either the first surface or the first processed end facet to the other across the edge therebetween, to evaluate the first processed end facet by means of the laser beam scanning. The group III nitride semiconductor crystal is exposed on the processed end facet. The step of evaluating the first processed end facet obtains, from the result of the laser beam scanning, angles of the processed end facet at plural positions located along the axial direction. The angle of the processed end facet is defined as an angle formed by the first processed end facet with a reference plane extending along the first surface.

In the method for evaluating an end facet for an optical cavity of a group III nitride semiconductor laser device according to yet another aspect of the present invention, the plural articles (e.g., a sample) are subjected to the process for forming an end facet for an optical cavity under the respective processing conditions to form the first processed end facet in each article, and then the first surface and the first processed end facet are relatively scanned with a laser beam to evaluate the first processed end facet through the reflected component of the laser beam. This evaluation can provide information on the changing angle of the first processed end facet with respect to the first surface (i.e., the verticality of the first processed end facet) through the laser beam scanning. The evaluation result allows a desired processing condition to be found on the basis of the plural processing conditions. With this desired processing condition, the substrate product is proceed to produce another substrate product and a laser bar from the aforementioned substrate product. This production method can provide a fabricating method, which can demonstrate the distribution of characteristics located at a quality close to a desired quality. This evaluation method can investigate the quality of the end facet in association with the processing conditions.

The method for evaluating an optical cavity end facet of a group III nitride semiconductor laser device further has the steps of (d) preparing a substrate with a primary surface formed from a group III nitride semiconductor; (e) preparing a substrate product including a semiconductor region, the substrate, and an electrode, the semiconductor region being grown on the primary surface of the substrate; and (f) after the evaluation, performing the processing of the substrate product under a desired processing condition determined based on the processing conditions, to form another substrate product and a laser bar from the substrate product. The laser bar has a first end facet formed through the processing, and the laser cavity of the group III nitride semiconductor laser device has the first end facet.

After examining the quality of the end facet in association with the processing condition, this evaluation method can perform the process on the substrate product under a desired processing condition, which is determined based on the processing condition, to produce another substrate product and a laser bar from the substrate product. This evaluation method can demonstrate the distribution of characteristics located at a quality close to a desired quality.

A method for evaluating a scribe groove used for forming an optical cavity end facet of a group III nitride semiconductor laser device according to yet another aspect of the present invention has the steps of: (a) irradiating a front surface of an article with a laser beam under a scribing-processing condition for use in an optical cavity of a group III nitride semiconductor laser device to form a scribe groove on the front surface, the article comprising a hexagonal group III nitride semiconductor crystal; (b) observing a cross-sectional shape of the scribe groove; (c) providing an estimation of a depth direction of the scribe groove on the basis of the cross-sectional shape, the scribe groove extends from the surface in the depth direction; and (d) obtaining a relationship between the depth direction of the scribe groove and the scribing-processing condition, based on a result of the estimation.

The method for evaluating a scribe groove can further comprises the steps of: (e) preparing a substrate with a primary surface of a group III nitride semiconductor; (f) preparing a substrate product including a semiconductor region, the substrate and an electrode, the semiconductor region being grown on the primary surface of the substrate; (g) after the estimation, forming a scribe groove in the substrate product under a scribing-processing condition determined on the basis of the scribing-processing condition; and (h) after the formation of the scribe groove, pressing the substrate product to form another substrate product and a laser bar. The laser bar includes a first end facet formed by pressing the substrate product, and a laser cavity of the group III nitride semiconductor laser device includes the first end facet.

The foregoing and other objects, features and advantages of the present invention will more easily be understood from the following detailed description of preferred embodiments of the present invention which are taken with the accompanying drawings.

Advantageous Effects of Invention

As described above, one aspect of the present invention provides a group III nitride semiconductor laser having a laser cavity, capable of reducing disturbance caused by return light, provided on a semipolar surface of a substrate in which a c-axis of the group-III nitride is inclined in the direction therefrom toward the direction of an m-axis thereof. Another aspect of the present invention provides a method for producing this group III nitride semiconductor laser.

Yet another aspect of the present invention provides a method for producing a group HI nitride semiconductor laser device, which is capable of adjusting the quality of an end facet which allows the emission, reflection, and/or transmission of a laser beam therefrom. Yet another aspect of the present invention provides a method for evaluating an end facet for the optical cavity of the group III nitride semiconductor laser device.

An additional aspect of the present invention provides a method for evaluating a scribe groove for use in the formation of an end facet for the optical cavity of the group III nitride semiconductor laser device.

BRIEF DESCRIPTION OF DRAWINGS

FIG. 2 is a view showing a polarization of emission from an active layer of the group III nitride semiconductor laser device;

FIG. 7 is a view showing the formation of scribe grooves;

FIG. 8 is a view showing the relationship between curves of scribe grooves and the scanning speed of a laser beam for processing;

FIG. 9 is a view showing an angle evaluation of a mirror for an optical cavity of a laser bar produced;

FIG. 11 is a view showing the verticality, evaluated by the method described with reference to FIG. 9, of an end facet of the laser bar produced under the condition (B);

DESCRIPTION OF EMBODIMENTS

The teachings of the present invention can be readily understood in view of the following detailed description with reference to the accompanying drawings presented for the illustrative purpose. Subsequently, embodiments of a group III nitride semiconductor laser device, a method for producing the group III nitride semiconductor laser device, a method for evaluating an optical cavity end facet of the group III nitride semiconductor laser device, and a method for evaluating a scribe groove according to the present invention will be described with reference to the accompanying drawings. The same portions are denoted by the same reference symbols as much as possible.

First Embodiment

Figure 1:
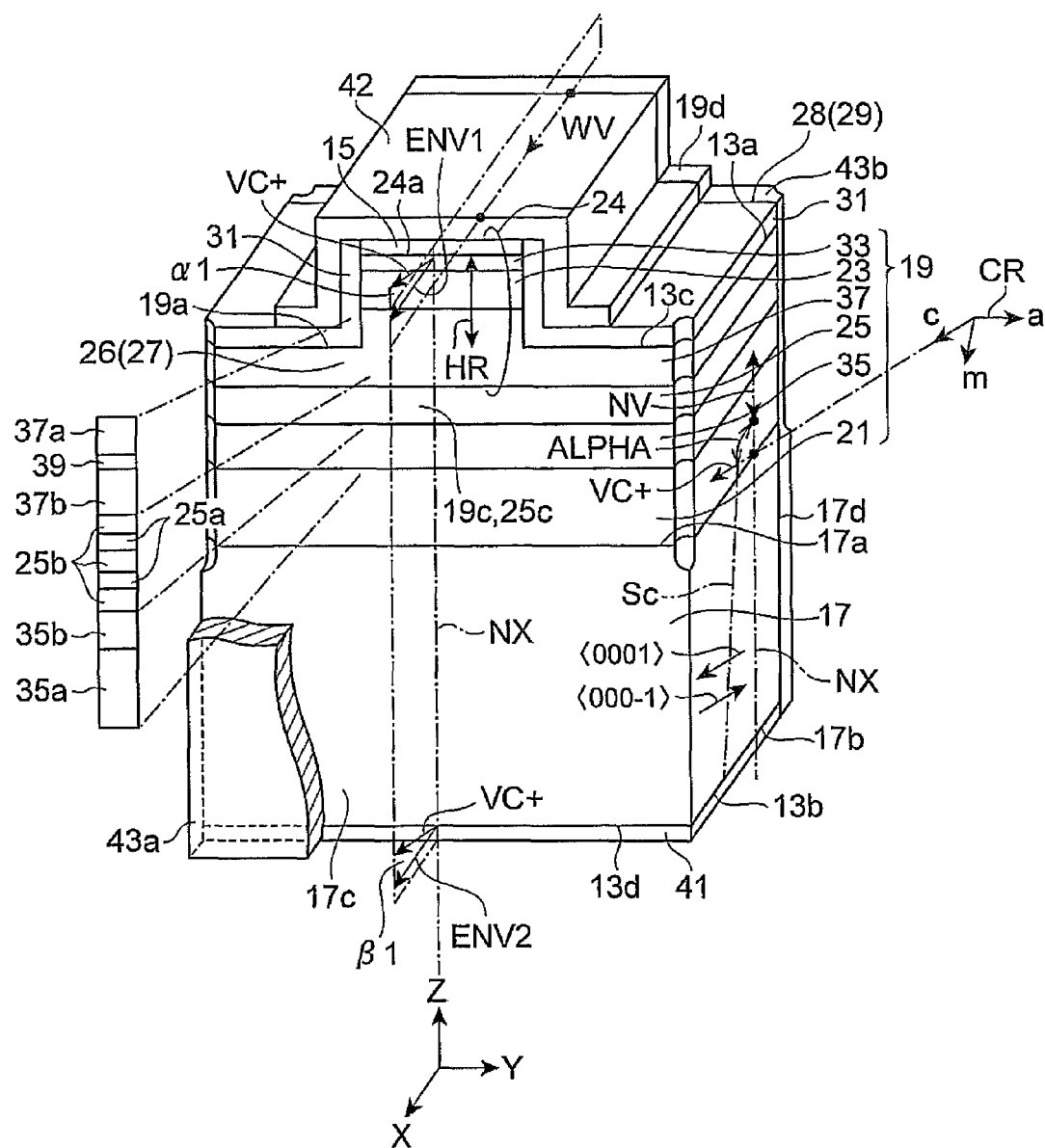
FIG. 1 is a schematic view showing a structure of a group III nitride semiconductor laser device according to the present embodiment.

FIG. 1 is a diagram schematically showing a structure of a group III nitride semiconductor laser device according to the present embodiment. The group III nitride semiconductor laser device 11 has a laser structure 13 and an ohmic electrode 15. The laser structure 13 includes a support base 17 and a semiconductor region 19. The support base 17 has a semipolar primary surface 17a, which comprises a hexagonal group III nitride semiconductor and a rear surface 17b. The semiconductor region 19 is provided on the semipolar primary surface 17a of the support base 17. The electrode 15 is provided on the semiconductor region 19 of the laser structure 13. The semiconductor region 19 includes an active layer 25, and the active layer 25 includes a gallium nitride based semiconductor layer.

A rectangular coordinate system S and a crystal coordinate system CR are depicted in FIG. 1. A normal axis NX is oriented in the direction of a Z-axis of the rectangular coordinate system S. The semipolar primary surface 17a extends parallel to a predetermined plane defined by X- and Y-axes of the rectangular coordinate system S. FIG. 1 also shows a typical c-plane Sc. In the present example, a +c axis vector (unit vector) representing the direction of a <0001> axis of the group III nitride semiconductor of the support base 17 is inclined with respect to a normal vector NV (unit vector) therefrom toward the direction of either one of the crystal axes; an m-axis or a-axis of the group III nitride semiconductor. The +c axis vector is represented as "+c axis vector VC+," and the direction of a <000-1> axis is opposite to the direction of the +c axis vector and represented as "−c axis vector VC−" (unit vector). In the example illustrated in FIG. 1, the +c axis vector VC+ of the hexagonal group III nitride semiconductor of the support base 17 is inclined at an angle ALPHA with respect to the normal axis NX toward the direction of a [−1010] axis of the hexagonal group III nitride semiconductor. This angle ALPHA is preferably equal to or greater than 71 degrees but equal to or less than 79 degrees.

The laser structure 13 includes a first end facet 27 and a second end facet 29 for a laser cavity. A laser waveguide for the laser cavity extends from the second end facet 29 to the first end facet 27 along the semipolar plane 17a, and a waveguide vector WV represents the direction from the second end facet 29 to the first end facet 27. The first and second end facets 27 and 29 of the laser structure 13 intersect with a reference plane defined by the crystal axis (e.g., the m-axis) of the group III nitride semiconductor and the normal axis NX. In FIG. 1, the first and second end facets 27 and 29 intersect with a m-n plane (a-n plane) defined by the normal axis NX and the m-axis (a-axis) of the hexagonal group III nitride semiconductor.

When the +c axis vector indicating the direction of the <0001> axis of the group III nitride semiconductor of the support base 17 is inclined at an angle equal to or greater 63 degrees but equal to or less than 80 degrees with respect to the normal vector NV indicating the direction of the normal axis NX therefrom toward the direction of the m-axis of the group III nitride semiconductor, the semipolar surface in this angular range can provide spatial uniformity of the indium composition in the group III nitride semiconductor containing indium and achieve high indium composition.

A first reflective film 43a for the optical cavity of the nitride semiconductor laser diode 11 is provided on a first end facet 19c of the semiconductor region 19. A second reflective film 43b for the optical cavity of the nitride semiconductor laser diode 11 is provided on a second end facet 19d of the semiconductor region 19.

An end facet 17c of the support base 17 and the end facet 19c of the semiconductor region 19 are exposed on each of the first and second end facets 27 and 29. The laser structure 13 includes a first surface (epi-surface) 13a and a second surface (the rear surface of the substrate) 13b. The first surface 13a is located on opposite side of the second surface 13b. The semiconductor region 19 is provided between the first surface 13a and the support base 17. A first normal vector ENV1 (unit vector) normal to the first end facet 27 is defined at a first edge 13c shared by the first end facet 27 and the first surface (epi-surface) 13a. The +c axis vector VC+ is inclined within the m-n plane at an angle α 1 with respect to the first normal vector ENV1 in the direction from the [−1010] axis of the group III nitride semiconductor to the c-axis thereof. A second normal vector ENV2 (unit vector) normal to the first end facet 27 is defined at a second edge 13d shared by the first end facet 27 and the second surface (the rear surface of the substrate) 13b. The +c axis vector VC+ is inclined within the m-n plane at an angle β1 with respect to the second normal vector ENV2 in the direction from the [−1010] axis of the group III nitride semiconductor to the c-axis thereof. The angle α1 is different from the angle β1. The angle α1 and the angle β1 have the same sign, whereas the absolute value of the angle α1 is greater than that of the angle β1. Angles for the second end facet 29 can be defined at the respective edges of the first and second surfaces 13a and 13b in a similar matter, and these angles can satisfy the equivalent angular relationship as the above. The first end facet 27 has a streaky structure extending in the direction of the cross product of the c-axis and the m-axis. The streaky structure includes steps each of which a low index plane and a non-low index plane and/or non-low index planes are arranged so as to be connected with each other to form. According to the observation by the inventors of the present invention, the streaky structure includes a step of, for example, 20 nm or less, in height.

According to this group III nitride semiconductor laser device 11, the angle α1 is different from the angle β1. In the first end facet 27 in the vicinity of the first surface 13a and near the epi-surface, the angle formed by the first normal line ENV1 and the +c axis vector VC+ is approximate to the angle α1 within the m-n plane. On the other hand, in the first end facet 27 in the vicinity of the substrate rear surface 17b, the angle formed by the second normal line ENV2 and the +c axis vector VC+ is approximate to the angle β1 within the m-n plane. In the angle ALPHA that is equal to or greater than 71 degrees and equal to or less than 79 degrees, when the angle α1 and the angle β1 have the same sign but the absolute value of the angle α1 is greater than the angle β1, the laser cavity capable of reducing disturbance caused by return light can be provided.

In addition, when the angle ALPHA is equal to or greater than 71 degrees but equal to or less than 79 degrees, it is preferred that the angle α1 be equal to or greater than 10 degrees but equal to or less than 25 degrees and that the angle β1 be equal to or greater than 0 degrees but equal to or less than 5 degrees. In this group III nitride semiconductor laser device 11, the angle α1 is different from the angle β1. In the first end facet 27 in the vicinity of the first surface 13a, e.g., near the epi-surface, since the angle ALPHA is equal to or greater than 71 degrees but equal to or less than 79 degrees, the angle formed by the first normal vector ENV1 and the +c axis vector VC+ within the m-n plane is approximate to the angle α1 (e.g., an angle equal to or greater than 10 degrees but equal to or less than 25 degrees). This angular range can provide the first end facet 27 near the first surface 13a with an angle favorable to the optical cavity. In the first end facet 27 in the vicinity of the substrate rear surface 17b, the angle formed by the second normal vector ENV2 and the +c axis vector VC+ within the m-n plane is approximate to the angle β1 (e.g., an angle equal to or greater than 0 degrees but equal to or less than 5 degrees). This angular range can provide the first end facet 27 near the second surface 13b with an angle greater than angles favorable to the optical cavity, because, at the angle ALPHA in the above angle range, the angle α1 and the angle β1 have the same sign and the absolute value of the angle α1 is greater than that of the angle β1. Therefore, reflection of light by the first end facet 27 in the vicinity of the first surface 13a, e.g., near the epi-surface, (an end face around an end facet of the active layer) can make a more significant contribution to lasing than the reflection of light by the first end facet 27 away from the first surface 13a, and the light that is reflected on the first end facet 27 away from the first surface 13a propagates in a direction different from the direction of the laser waveguide and accordingly does not work as the source of noise. In the present example, an angle ($\alpha$1+ALPHA) can be 81 to 104 degrees, and an angle ($\beta$1+ ALPHA) can be 71 to 84 degrees. Angles for the second end facet 29 can be defined at the respective edges of the first and second surfaces 13a and 13b in a similar matter, and these angles can satisfy the equivalent angular relationship as the one described above.

The semiconductor region 19 includes a first cladding layer 21 and a second cladding layer 23. The active layer 25 is provided between the first cladding layer 21 and the second cladding layer 23. The first cladding layer 21 is made of a gallium nitride based semiconductor of the first conductivity type, such as n-type AlGaN, n-type InAlGaN, or the like. The second cladding layer 23 is made of a gallium nitride based semiconductor of the second conductivity type, such as p-type AlGaN, p-type InAlGaN, or the like. The gallium nitride based semiconductor layers in the active layer 25 are, for example, well layers 25a. The active layer 25 includes barrier layers 25b made of a gallium nitride based semiconductor, and the well layers 25a and the barrier layers 25b are arranged alternately in the direction of the z-axis. The well layers 25a are each made of, for example, InGaN or the like, and the barrier layers 25b are each made of, for example, GaN, InGaN, or the like. The active layer 25 can include a light emitting region, such as a quantum well structure, which is provided to generate light of a wavelength equal to or greater than 360 nm but equal to or less than 600 nm. The use of the semipolar plane can allow the active layer 25 to emit light of a wavelength equal to or greater than 430 nm but equal to or less than 550 nm. The active layer 25 can also generate green light of wavelength range, such as light of a wavelength equal to or greater than 500 nm but equal to or less than 550 nm. The first cladding layer 21, the second cladding layer 23, and the active layer 25 are arranged along the normal axis NX of the semipolar primary surface 17a. The normal axis NX extends in the direction of the normal vector NV. A c-axis Cx of the group III nitride semiconductor of the support base 17 extends in the direction of the +c axis vector VC+.

The +c axis vector VC+ has a normal component in the direction of the axis NX normal to the semipolar primary surface 17a, and a parallel component in a direction parallel to the semipolar primary surface 17a. The laser structure 13 includes a laser waveguide structure extending on the semipolar primary surface 17a of the support base 17. The parallel component of the +c axis vector VC+ is oriented in the direction from the second end facet 29 to the first end facet 27, and the laser waveguide structure extends in the direction of the parallel component of the +c axis vector VC+. According to this group III nitride semiconductor laser device 11, when the parallel component of the +c axis vector VC+ is oriented in the direction from the second end facet 29 to the first end facet 27, the first end facet 27 satisfies as follows: the angle formed by a support base end facet 17a and the parallel component of the +c axis vector VC+ is greater than the angle formed by an epi-end facet and the parallel component of the +c axis vector.

The first cladding layer 21, the second cladding layer 23, and the active layer 25 are grown epitaxially on the semipolar primary surface 17a, and arranged along the direction of the normal component of the +c axis vector VC+. The first cladding layer 21, the second cladding layer 23, and the active layer 25 extend in the direction of the parallel component of the +c axis vector VC+. The first cladding layer 21, the second cladding layer 23, and the active layer 25 can form the laser waveguide structure extending on the semipolar primary surface 17a of the support base 17. In this structure, since the first cladding layer 21, the second cladding layer 23, and the active layer 25 are epitaxially grown on the semipolar primary surface 17a to be arranged along the direction of the normal component of the +c axis vector VC+, and the crystal axis of the semiconductor region 19 are associated with the crystal axis of the support base 17. This association between the directions of the +c axis vector VC+ in the semiconductor region 19 and the support base 17 enables high-quality formation of end facets.

The group III nitride semiconductor laser device 11 also has an insulating film 31. The insulating film 31 is provided on a top surface 19a of the semiconductor region 19 of the laser structure 13 so as to cover the top surface 19a. The semiconductor region 19 is located between the insulating film 31 and the support base 17. The support base 17 is made of a hexagonal group III nitride semiconductor. The insulating film 31 has an opening 31a. The opening 31a is formed into, for example, a stripe shape. When the c-axis is inclined toward the direction of the m-axis (a-axis) as in the present example, the opening 31a extends in the direction of the line of intersection formed by the top surface 19a of the semiconductor region 19 and the m-n plane (a-n plane) as described above. The line of intersection is oriented in the direction of the waveguide vector WV.

The electrode 15 is in contact with the top surface 19a of the semiconductor region 19 (e.g., a contact layer 33 of the second conductivity type) via the opening 31a and extends in the direction of the above-described line of intersection. In the group III nitride semiconductor laser device 11, the laser waveguide includes the first cladding layer 21, the second cladding layer 23 and the active layer 25, and extends in the direction of the above-described line of intersection.

The group III nitride semiconductor laser device 11 can have a gain waveguide structure. The electrode 15 is in contact with the top surface of the semiconductor region 19 via the opening 31a of the insulating film 31. The angle $\alpha$1 and the angle $\beta$1 are defined on an axis extending perpendicular to the semipolar primary surface 17a of the support base 17 and passing through the center of the width of the electrode 15 and the width of the opening 31a of the insulating film 31 that define the gain waveguide structure. The direction of the opening 31a or the direction of the electrode 15 can define the direction of the gain waveguide.

Moreover, a laser diode with a ridge structure 24 can be applied to the group III nitride semiconductor laser device 11. The group III nitride semiconductor laser device 11 is configured in such a manner that, for example, the semiconductor region 19 of the laser structure 13 has the ridge structure 24. The electrode 15 is in contact with an upper surface 24a of the ridge structure 24. The angle $\alpha$1 and the angle $\beta$1 are defined on an axis that passes through the center of the width of the upper surface 24a of the ridge structure 24 and is orthogonal to the semipolar primary surface 17a of the support base 17. The ridge structure 24 can control the distribution width of current supplied to the active layer 25, as well as optical confinement, and adjust the degree of an interaction between carriers and light which travels in the laser waveguide.

In the group III nitride semiconductor laser device 11, the semiconductor region 19 includes the contact layer 33 made of group III nitride and an optical guiding layer 37 made of a group III nitride. The optical guiding layer 37 is provided between the active layer 25 and the contact layer 33, and between the active layer 25 and the cladding layer 23. The ridge structure 24 preferably has a height HR allowing the contact layer 33 and a part of the optical guiding layer 37 to be contained therein. The height HR of the ridge structure 24 guides current, which is to be supplied to the active layer 25, to facilitate adjustment of the width of current distribution in the active layer 25.

Another electrode 41 is provided on the rear surface 17b of the support base 17, and the electrode 41 covers, for example, the rear surface 17b of the support base 17. The group III nitride semiconductor laser device 15 can further have a pad electrode 42, which is provided on the ohmic electrode 15. The pad electrode 42 can be made of gold, for example, and the ohmic electrode 15 is in contact with the top surface 19a of the semiconductor region 19 and preferably includes, for example, a Pd electrode.

In the group III nitride semiconductor laser device 11, the support base 17 has a first base end facet 17c, and the base end facet 17c is connected to the end facet 19c of the semiconductor region 19. The first reflective film 43a is provided on the first base end facet 17c. The support base 17 has a second base end facet 17d, and the base end facet 17d is connected to the end facet 19d of the semiconductor region 19. The second reflective film 43b is provided on the second base end facet 17d. In this embodiment, the first reflective film 43a and the second reflective film 43b extend in a continuous manner from the first end facet 19c and the second end facet 19d of the semiconductor region 19 to the first base end facet 17c and the second base end facet 17d, respectively.

The first reflective film 43a and the second reflective film 43b each can be composed of, for example, a dielectric multilayer film. In the following description, the first reflective film 43a and the second reflective film 43b are referred to as a first dielectric multilayer film 43a and a second dielectric multilayer film 43b, respectively.

In the group III nitride semiconductor laser device 11, the first end facet 27 and the second end facet 29 each can include an end face which is not formed by cleavage. In order to distinguish the first end facet 27 and the second end facet 29 from a cleavage plane with a low-index plane in the present specification, the first end facet 27 and the second end facet 29 are referred to as a first fractured face 27 and a second fractured face 29, respectively. The first fractured face 27 and the second fractured face 29 intersect with the m-n plane (a-m plane) that is defined by the normal axis NX and the m-axis (a-axis) of the hexagonal group III nitride semiconductor. The laser cavity of the group III nitride semiconductor laser device 11 includes the first and second fractured faces 27 and 29, and the laser waveguide extends from either one of the first and second fractured faces 27 and 29 to the other. The laser structure 13 includes the first surface 13a and the second surface 13b, and the first surface 13a is located on opposite side of the second surface 13b. The first and second fractured faces 27 and 29 extend from the edge 13c of the first surface 13a to the edge 13d of the second surface 13b. The first and second fractured faces 27 and 29 are different from a typical cleavage plane, such as the c-plane, m-plane and a-plane.

According to this group III nitride semiconductor laser device 11, the first and second fractured faces 27 and 29 forming the laser cavity intersect with the m-n plane. Accordingly, the laser waveguide can be provided to extend in the direction of the line of intersection of the m-n plane with the semipolar primary surface 17a. The group III nitride semiconductor laser device 11 has a laser cavity capable of demonstrating a low threshold current.

The optical waveguide structure of the group III nitride semiconductor laser device 11 is now described in detail. The group III nitride semiconductor laser device 11 includes an n-side optical guiding layer 35 and a p-side optical guiding layer 37. The n-side optical guiding layer 35 includes a first portion 35a and a second portion 35b. The n-side optical guiding layer 35 is made of, for example, GaN, InGaN, or the like. The p-side optical guiding layer 37 includes a first portion 37a and a second portion 37b. The p-side optical guiding layer 37 is made of, for example, GaN, InGaN, or the like. A carrier blocking layer 39 is provided between, for example, the first portion 37a and the second portion 37b.

FIG. 2 is a diagram showing the polarization of light emitted by the active layer 25 of the group III nitride semiconductor laser device 11. As shown in FIG. 2, the dielectric multilayer films 43a and 43b are provided on the first and second end facets 27 and 29, respectively.

As shown in part (b) of FIG. 2, a laser beam L from the active layer 25 in the laser waveguide, directed in the direction of the crystal axis of the present embodiment (along the m-n plane), is polarized in the direction of the a-axis of the hexagonal group III nitride semiconductor. In this group III nitride semiconductor laser device 11, a band-to-band transition that can demonstrate a low threshold current has polarization properties. The first and second end facets 27 and 29 for the laser cavity are different from the typical cleavage planes, such as the c-plane, m-plane and a-plane. The first and second end facets 27 and 29, however, have flatness and verticality sufficient to acting as a mirror for a laser cavity. Using the first and second end facets 27 and 29 and the laser waveguide extending between the end facets 27 and 29 can demonstrate lasing with a low-threshold, as shown in part (b) of FIG. 2, by use of a light component I1 created by the transition that is stronger than the of a light component I2 that is polarized in the direction of a projected component of the c-axis onto the primary surface. Light in LED-mode in the group III nitride semiconductor laser device 11 includes a polarization component I1 in the direction of the a-axis of the group III nitride semiconductor and a polarization component I2 in the direction indicated by the projected c-axis of the group III nitride semiconductor onto the primary surface, and the polarization component I1 is greater than the polarization component I2.

In the group III nitride semiconductor laser device 11, the end facet 17c of the support base 17 and the end facet 19c of the semiconductor region 19 appear on each of the first end facet 27 and the second end facet 29, and the end facet 17c and the end facet 19c are covered with the dielectric multilayer film 43a. An angle GAMMA, which is formed by an m-axis vector MA of the active layer 25 and a normal vector NA of an end facet 25c of the active layer 25 or the end facet 17c of the support base 17 includes a component $(GAMMA)_1$ that is defined in a first plane S1 defined by the c-axis and m-axis of the group III nitride semiconductor, and a component $(GAMMA)_2$ that is defined in a second plane S2 perpendicular to the first flat plane S1 and the normal axis NX. The component $(GAMMA)_1$ is preferably equal to or greater than (ALPHA−5) degrees and equal to or less than (ALPHA+5) degrees in the first plane S1, which is defined by the c-axis and m-axis of the group III nitride semiconductor. This angular range is understood as that for an angle to be formed by the m-plane and a reference surface extending along the end facet 25c of the active layer 25. This group III nitride semiconductor laser device 11 has an end facet satisfying the above-described verticality as to the angle GAMMA, which is taken in the direction from one of the c-axis and the m-axis to the other. Furthermore, the component $(GAMMA)_2$ is preferably equal to or greater than −5 degrees and equal to or less than +5 degrees in the second plane S2. Here, $GAMMA_2 = (GAMMA)_1^2 + (GAMMA)_2^2$ is established. The end facets 27 and 29 of the group III nitride semiconductor laser device 11 satisfy the aforementioned verticality as to the angle defined in a plane perpendicular to the normal axis NX of the semipolar plane 17a.

Figure 3:
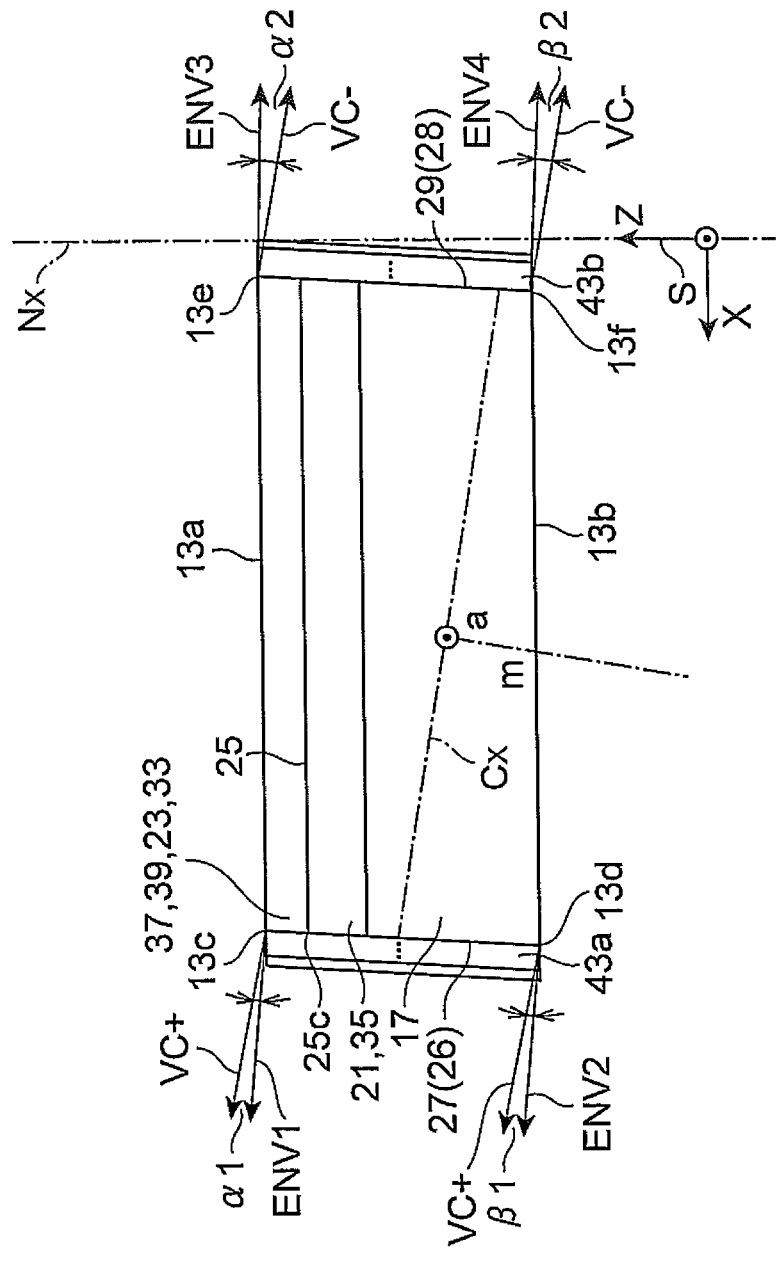
FIG. 3 is a schematic cross sectional view, taken along a plane defined by the c-axis and the m-axis thereof, showing a device.

FIG. 3 is a diagram schematically showing the cross section, taken along a plane defined by the c-axis and the m-axis, in the direction in which the laser waveguide extends. FIG. 3 shows the relationship between the angle α1 and the angle β1 in the first end facet 27 described above. The angle α1 is associated with the inner product of the vector ENV1 and the +c axis vector VC+. The angle β1 is associated with the inner product of the vector ENV2 and the +c axis vector VC+.

In the group III nitride semiconductor laser device 11, the −c axis of the group III nitride semiconductor of the support base 17 points to the direction opposite to the direction of the <000-1> axis. A third normal vector ENV3 (unit vector) normal to the second end facet 29 is defined at a third edge 13e where the second end facet 29 and the first surface (epi-surface) 13a meet, and the direction of the <000-1> axis is represented by the −c axis vector VC−. The −c axis vector VC− is inclined at an angle α2 with respect to the third normal vector ENV3 within the m-n plane in the direction from the [−1010] axis of the group III nitride semiconductor of the support base 17 to the c-axis. It is preferred that the angle α2 be, for example, equal to or greater than +10 but equal to or less than +25 degrees.

A fourth normal vector ENV4 (unit vector) of the second end facet 29 is defined at a fourth edge 13f where the second end facet 29 and the second surface (substrate rear surface) 13b meet. The −c axis vector VC− is inclined at an angle β2 with respect to the fourth normal vector ENV4 within the m-n plane in the direction from the [−1010] axis of the group III nitride semiconductor of the support base 17 to the c-axis. It is preferred that the angle β2 be, for example, equal to or greater than 0 degrees but equal to or less than +5 degrees.

According to this group III nitride semiconductor laser device 11, the angle α2 is different from the angle β2. In the second end facet 29 in the vicinity of the first surface 13a, e.g., near the epi-surface, the angle formed by the third normal vector ENV3 and the −c axis vector VC− in the m-n plane is approximate to the angle α2 (e.g., equal to or greater than 10 degrees but equal to or less than 25 degrees). This angular range provides the second end facet 29 in the vicinity of the first surface 13a with an angle favorable to the optical cavity because of the angle ALPHA equal to or greater than 71 degrees and equal to or less than 79 degrees. In the second end facet 29 in the vicinity of the substrate rear surface 17b, the angle formed by the fourth normal vector ENG4 and the −c axis vector VC− in the m-n plane is approximate to the angle β2 (e.g., equal to or greater than 0 degrees but equal to or less than 5 degrees). Reflection of light by the second end facet 29 in the vicinity of the first surface 13a, e.g., near the epi-surface (an end facet area around an end facet of the active layer), makes a more significant contribution to lasing than reflection of light by the second end facet 29 away from the first surface 13a. Since the angle α2 and the angle 132 have the same sign and the absolute value of the angle α2 is greater than that of the angle β2, the angle ALPHA provides the second end facet 29 in the vicinity of the second surface 13b with an angle greater than angles favorable to the optical cavity.

Referring to FIG. 1 again, it is preferred that the thickness of the support base 17 be equal to or less than 400 μm in the group III nitride semiconductor laser device 11. This group III nitride semiconductor laser device is favorable for providing fractured faces for an excellent laser cavity. It is more preferred that the thickness of the support base 17 be equal to or less than 100 μm in the group III nitride semiconductor laser device 11. This group III nitride semiconductor laser device 11 is even more favorable for providing fractured faces for an excellent laser cavity. A thickness of 50 μm or more can demonstrate easy handling of the group III nitride semiconductor laser device and improve the production yield.

In the group III nitride semiconductor laser device 11, cleavage planes, which are represented by a low-plane index, cannot be used as an end facet for the laser cavity. In this specification, such end facet is referred to as "fractured face" in order to distinguish it from the cleavage planes. According to the teaching provided by the inventors, it is preferred that the angle formed by the normal axis NX and the c-axis of the hexagonal group III nitride semiconductor be equal to or greater than 45 degrees but equal to or less than 80 degrees in order to use a fractured face and that this angle be equal to or greater than 100 degrees but equal to or less than 135 degrees. When the angle is less than 45 degrees or exceeds 135 degrees, it is highly likely that an end facet formed by means of pressing is composed of the m-plane. When the angle exceeds 80 degrees and is less than 100 degrees, desired flatness and verticality might not be obtained.

In the group III nitride semiconductor laser device 11, from the perspective of forming the fractured face, it is preferred that the angle ALPHA formed by the normal axis NX and the c-axis of the hexagonal group III nitride semiconductor be equal to or greater than 71 degrees but equal to or less than 79 degrees. When the angle is less than 71 degrees, the guide-effect resulting from c-plane cleavage cannot be used for breakage, resulting in degradation of the flatness and verticality of the fractured face. On the other hand, when the angle exceeds 79 degrees, it might not be possible to obtain a laser cavity capable of reducing disturbance caused by return light.

In the group III nitride semiconductor laser device 11, when the c-axis of the group III nitride semiconductor is inclined in the direction of the m-axis of the nitride semiconductor, practical plane orientation and angular range include at least the following orientations and angular ranges. For example, the primary surface 17a of the support base 17 can be inclined with respect to the {20-21} plane at an angle in a range of equal to or greater than −4 degrees but equal to or less than +4 degrees. The primary surface 17a of the support base 17 can also be the {20-21} plane.

In the group III nitride semiconductor laser device 11, the inclination angle ALPHA is preferably equal to or greater than 71 degrees. When the inclination angle ALPHA is less than 71 degrees, the guide-effect resulting from c-plane cleavage cannot work in breakage, resulting in degradation in the flatness and verticality of the fractured face. Also, the inclination angle ALPHA is preferably equal to or greater than 79 degrees. When the inclination angle ALPHA exceeds 79 degrees, it might not be possible to obtain a laser cavity capable of reducing disturbance caused by return light.

The support base 17 can be made of GaN, AlN, AlGaN, InGaN, or InAlGaN. The use of a substrate made of any of these gallium nitride based semiconductors can produce the fractured faces 27 and 29 that can be used as laser cavity.

The primary surface 17a of the support base 17 can be made of GaN, and the support base 17 can be a GaN single crystal substance. According to this group III nitride semiconductor laser device, making the laser structure using the GaN primary surface can demonstrate emission of light having, for example, the wavelength range described above (wavelength range from blue to green). The use of an AlN substrate or an AlGaN substrate can not only increase the polarization degree but also enhance the optical confinement effect by providing a low refractive index thereof. The use of an InGaN substrate can reduce the ratio of lattice mismatch between the substrate and a light emitting layer, thereby improving the crystal quality. Moreover, in the group III nitride semiconductor laser device 11, the support base 17 can have a stacking fault density of $1\times10^4$ cm$^{-1}$ or lower. The stacking fault density of $1\times10^4$ cm$^{-1}$ or lower is unlikely to fortuitously degrade the flatness and/or verticality of the optical cavity made of end facets.

Figure 4:
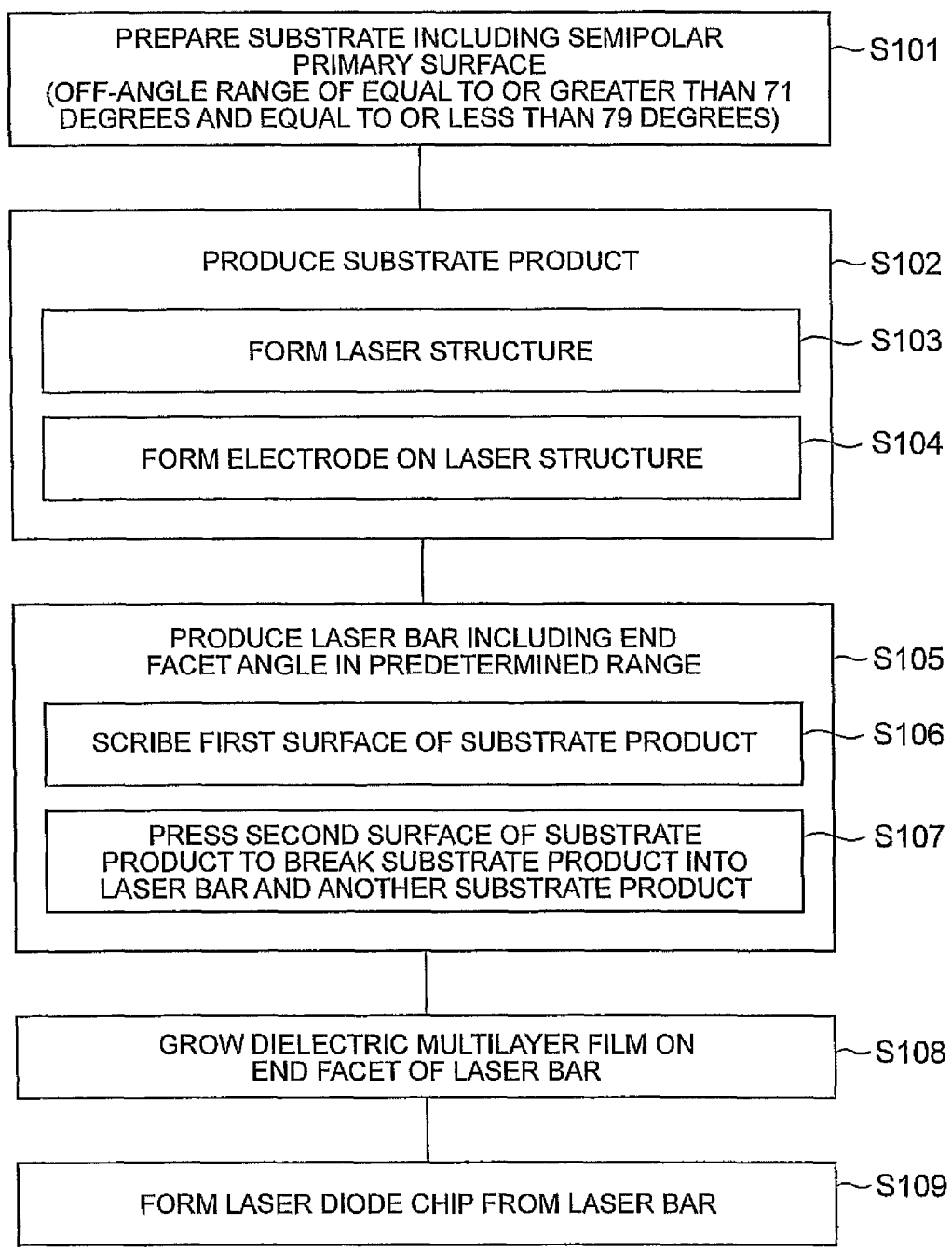
FIG. 4 is a view showing primary steps in a method for producing the group III nitride semiconductor laser device according to the present embodiment.

FIG. 4 is a diagram showing main steps of a method for producing the group III nitride semiconductor laser device according to the present embodiment. Referring to part (a) of FIG. 5, a substrate 51 is shown. In the example, a c-axis of the substrate 51 is inclined therefrom toward the direction of an m-axis thereof. Step S101 prepares the substrate 51 for producing a group III nitride semiconductor laser device. The c-axis (vector VC+) of a hexagonal group III nitride semiconductor of the substrate 51 is inclined at a non-zero angle ALPHA with respect to the normal axis NX toward the direction of the m-axis (vector VM) of the hexagonal group III nitride semiconductor. Accordingly, the substrate 51 has a semipolar primary surface 51a made of the hexagonal group III nitride semiconductor. In the fabricating method according to the present embodiment, the angle ALPHA of the primary surface 51a can be, for example, not less than 71 degrees and not more than 79 degrees.

Figure 5:
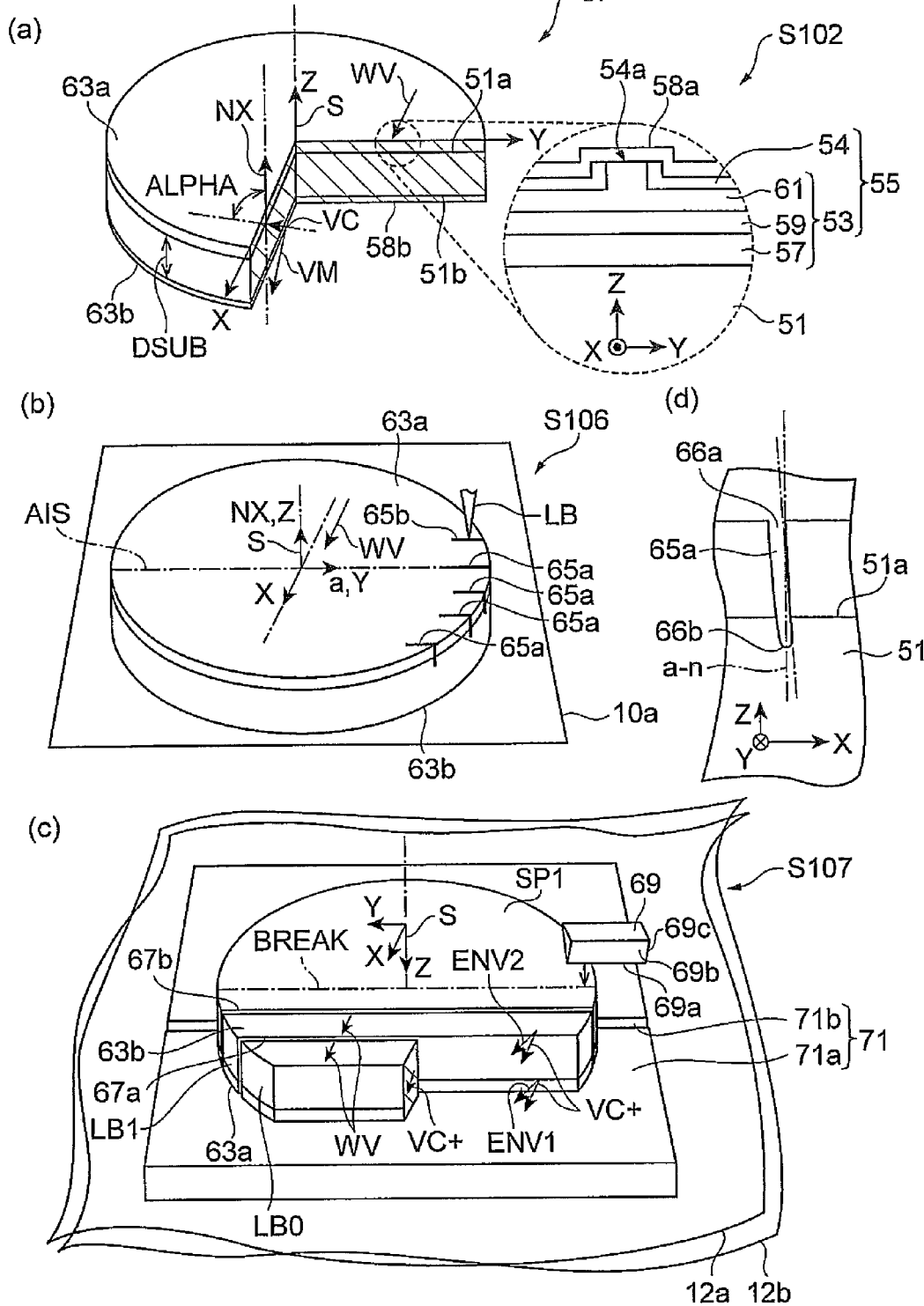
FIG. 5 is a schematic view showing primary steps of the method for producing the group III nitride semiconductor laser device according to the present embodiment.

In step S102, the fabrication of a substrate product SP is carried out. Part (a) of FIG. 5 illustrates the substrate product SP as a member that is in a substantially disc shape, but the shape of the substrate product SP is not limited to this shape.

In order to obtain the substrate product SP, first, step S103 forms a laser structure 55. The laser structure 55 includes a semiconductor region 53 and the substrate 51. The semiconductor region 53 is formed on the semipolar primary surface 51a. In order to form the semiconductor region 53, a gallium nitride based semiconductor region 57 of the first conductivity type, a light emitting layer 59, and a gallium nitride based semiconductor region 61 of the second conductivity type are grown sequentially on the semipolar primary surface 51a. The gallium nitride based semiconductor region 57 can include, for example, an n-type cladding layer, and the gallium nitride based semiconductor region 61 can include, for example, a p-type cladding layer. The light emitting layer 59 is provided between the gallium nitride based semiconductor region 57 and the gallium nitride based semiconductor region 61 and can include an active layer, an optical guiding layer, an electron blocking layer, and the like. The gallium nitride based semiconductor region 57, the light emitting layer 59, and the gallium nitride based semiconductor region 61 of the second conductivity type are arranged along the normal axis NX of the semipolar primary surface 51a. These semiconductor layers are grown epitaxially on the primary surface 51a. The semiconductor region 53 is covered with an insulating film 54. The insulating film 54 is made of, for example, silicon oxide. The insulating film 54 has an opening 54a. The opening 54a has a shape of, for example, a stripe. Part (a) of FIG. 5 shows the waveguide vector WV, and, in the present example, this vector WV extends parallel to the m-n plane. If needed, a ridge structure may be formed in the semiconductor region 53 prior to forming the insulating film 54, or the ridge structure may be formed in the semiconductor region 53 at the same time as forming the insulating film 54. The ridge structure may also be formed in the semiconductor region 53 at the same time as forming the insulating film 54 and an electrode. The ridge structure formed in this manner can include the gallium nitride based semiconductor region 61 that is ridge-shaped. The thickness of the semiconductor region 53 can be, for example, 3 to 4 μm.

In Step S104, an anode electrode 58a and a cathode electrode 58b are formed on the laser structure 55. Prior to forming an electrode on a back side of the substrate 51, the rear surface of the substrate on the primary surface of which crystals have been grown is polished to form the substrate product SP having a desired thickness DSUB. In the electrode formation, the anode electrode 58a, for example, is formed on the semiconductor region 53, and the cathode electrode 58b on the rear surface (polished surface) 51b of the substrate 51. The anode electrode 58a extends in the direction of the X-axis, and the cathode electrode 58b covers the entire rear surface 51b. The substrate product SP is formed through the above steps. The substrate product SP includes a first surface 63a and a second surface 63b, and the second surface 63b is provided on opposite side of the first surface 63a. The semiconductor region 53 is located between the first surface 63a and the substrate 51.

In the subsequent step S105, a laser bar is formed, and has laser cavity end facets. The end facets each have an end facet angle in a predetermined range. In the present example, the laser bar is produced out of the substrate product SP. The laser bar has a pair of end facet on which the respective dielectric multilayer films can be formed. An example of producing the laser bar and end facets is described below.

In step S106, as shown in part (b) of FIG. 5, scribe grooves are formed on the first surface 63a of the substrate product SP. The c-axis of the hexagonal group III nitride semiconductor of the substrate 51 is oriented in the direction of the <0001> axis. The direction of the <0001> axis is indicated by the +c axis vector. In the present embodiment, scribing is preferably carried out in a direction intersecting with the +c axis vector. In addition, a laser scriber 10a can be used to perform the scribing. As a result of the scribing, scribe grooves 65a are formed thereon. Referring to part (b) of FIG. 5, five scribe grooves are already formed, and a laser beam LB is now used to form a scribe groove 65b. The length of each scribe groove 65a is shorter than the length of the line of intersection MS where the first surface 63a and the a-n plane defined by the a-axis and the normal axis NX of the hexagonal group III nitride semiconductor meet, and the first surface 63a is irradiated with the laser beam LB in parts of the line of intersection MS. The radiation of the laser beam LB can form, on the first surface 63a, a groove that extends in a certain direction and reaches the substrate in depth. The scribe grooves 65a can be formed at, for example, an edge of the substrate product SP and one or more scribe grooves may be formed so as to be arranged at a pitch corresponding to the width of a laser chip.

The scribe grooves 65a are formed through the execution of the scribing, and the scribe grooves 65a reach the substrate 51 from the front surface of the semiconductor region 53. As shown in part (d) of FIG. 5, each scribe groove 65a has an opening 66a in the front surface of the semiconductor region 53, and a bottom portion 66b located in the substrate 51. The end of the opening 66a of the scribe groove 65a and the deepest end of the bottom portion 66b of the scribe groove 65a define a reference plane, which can extend in the direction of the a-n plane defined by the normal axis NX and the a-axis of the group III nitride semiconductor, and it is preferred that the scribe grooves 65a be substantially parallel thereto without curving in the depth direction. The direction in which each scribe groove 65a may curve is associated with the direction of inclination of the c-axis. Reducing the curves of the scribe grooves 65a helps control shapes for the end facets 67a and 67b.

In step S107, as shown in part (c) of FIG. 5, the substrate product SP is placed between sheets 12a and 12b, and then presses the second surface 63b of the substrate product SP to break the substrate product SP into another substrate product SP1 and a laser bar LB1. The pressing of the substrate product SP is performed using a breaking device such as a blade 69. The blade 69 includes an edge 69a extending in one direction and at least two blade faces 69b and 69c that define the edge 69a. The pressing of the substrate product SP1 is also performed on a support device 71. The support device 71 includes a supporting surface 71a and a recess portion 71b, and the recess portion 71b extends in one direction. The recess portion 71b is formed in the supporting surface 71a. The position and direction of the arrangement of the scribe grooves 65a in the substrate product SP1 are oriented in the direction in which the recess portion 71b of the support device 71 extends, and the substrate product SP1 is positioned to the recess portion 71b on the support device 71. The direction of the edge of the breaking device is oriented in the direction in which the recess portion 71b extends, and then the edge of the breaking device presses against the substrate product SP1 in a direction toward the second surface 63b. It is preferred that the direction toward the second surface 63b be substantially perpendicular to the second surface 63b. These steps allows the substrate product SP to be separated into the substrate product SP1 and the laser bar LB1. Pressing the breaking device against the substrate product forms the laser bar LB1 having the first and second end facets 67a and 67b. In the end facets 67a and 67b, at least part of the light emitting layer is vertical and smooth enough that these end facets can form lasing mirrors for the semiconductor laser.

The laser bar LB1 thus created has the first and second end facets 67a and 67b, which have been formed by separating the substrate product SP. Each of the end facets 67a and 67b extends from the first surface 63a to the second surface 63b. The end facets 67a and 67b, therefore, can configure the laser cavity of the group III nitride semiconductor laser device and intersect with an XZ plane. This XZ plane corresponds to the m-n plane defined by the m-axis of the group III nitride semiconductor and the normal axis NX. The waveguide vector WV is shown in each of the laser bars LB0 and LB1. The waveguide vector WV extends in the direction from the end facet 67b to the end facet 67a. In part (c) of FIG. 5, the laser bar LB0 is shown in a partially broken view in order to show the direction of the c-axis vector VC. The waveguide vector WV forms an acute angle with the c-axis vector VC+.

The first and second end facets 67a and 67b each extend from the edge of the first surface 63a to the edge of the second surface 63b. The first normal vector ENV1 of the first end facet 67a is defined at the edge where the first end facet 67a and the first surface (epi-surface) 63a meet. The +c axis vector VC+ forms an angle $\alpha 1$, which is defined within the m-n plane in a direction from the [−1010] axis of the group III nitride semiconductor toward the c-axis, with the first normal vector ENV1. The second normal vector ENV2 of the first end facet 67a is defined at the edge where the first end facet 67a and the second surface (substrate rear surface) 63b meet. The +c axis vector VC+ forms an angle $\beta 1$, which is defined within the m-n plane in the direction from the [−1010] axis of the group III nitride semiconductor toward the c-axis, with the second normal vector ENV 2.

It is preferred that the scribing and breaking be performed in such a manner that the angle $\alpha 1$ falls within the range of 10 degrees to 25 degrees and that the angle $\beta 1$ falls within the range of 0 degrees to 5 degrees.

According to this production method, the angle $\alpha 1$ is different from the angle $\beta 1$. In the first end facet 67a in the vicinity of the first surface 67a, e.g., near the epi-surface, the angle formed by the normal vector ENV1 and the c-axis is approximate to the angle $\alpha 1$ (e.g., equal to or greater than 10 degrees but equal to or less than 25 degrees) within the m-n plane. This angular range provides the first end facet 67a in the vicinity of the first surface 63a with an angle favorable to an optical cavity because the angle ALPHA is equal to or greater than 71 degrees but equal to or less than 79 degrees. On the other hand, in the first end facet 67a in the vicinity of the rare surface 63b of the substrate, the angle formed by the second normal vector ENV2 and the c-axis is approximate to the angle $\beta$ (e.g., equal to or greater than 0 degrees but equal to or less than 5 degrees) within the m-n plane. Reflection of light by the part of the first end facet (an end face around the end facet of the active layer) 67a in the vicinity of the first surface 63a and near the epi-surface, makes a more significant contribution to lasing than reflection of light in the part of the first end facet 67a away from the first surface 63a and close to the second surface 63b. Since the angle $\alpha 1$ and the angle $\beta 1$ have the same sign and the angle $\alpha 1$ is larger than the angle $\beta 1$, the angle ALPHA in the above range allows the first end facet 67a in the vicinity of the second surface 63b to have an angle that is larger than angles favorable to the optical cavity.

Further, this method carries out as follows: the first surface 63a of the substrate product SP is scribed in the direction of the a-axis of the hexagonal group III nitride semiconductor; and thereafter the second surface 63b of the substrate product SP is pressed to break the substrate product SP into the new substrate product SP1 and laser bar LB1. This process sequence allows the first and second end facets 67a and 67b to be formed in the laser bar LB1 in such a manner as to intersect with the m-n plane. This formation of end facets can provide the first and second end facets 67a and 67b with enough flatness and verticality to form the laser cavity of the group III nitride semiconductor laser device. The laser waveguide therein extends in the direction of inclination of the c-axis of the hexagonal group-III nitride. This method forms mirror end facets for a laser cavity demonstrating the laser waveguide oriented as above.

According to this method, the substrate product SP1 is broken into the new substrate product SP1 and laser bar LB1. In step S107, breaking the substrate product by pressing it is repeatedly carried out to produce plural laser bars. The scribe grooves 65a shorter than a break line BREAK for the laser bar LB1 is used to cause the fracture of the substrate product.

In step S108, a dielectric multilayer film is formed on each of the end facets 67a and 67b of the laser bar LB1 to form a laser bar product. This step is carried out, for example, in the following manner. First of all, a dielectric multilayer film is formed on either one of the end facets 67a and 67b of the laser bar LB1. Next, another dielectric multilayer film is formed on the other of the end facets 67a and 67b of the laser bar LB1. When the reflectivity of the dielectric multilayer film on the front side is lower than the reflectivity of the dielectric multilayer film on the rear side, this front side emits most of the laser beam therefrom, while the rear side reflects most of the laser beam.

In step S109, this laser bar product is separated into individual semiconductor laser chips.

The substrate 51 can be made of GaN, AlN, AlGaN, InGaN, or InAlGaN. The use of the substrate made of any of these gallium nitride based semiconductors results in obtaining the end facets that can be used as the laser cavity. It is preferred that the substrate 51 be made of GaN.

In the formation of the substrate product SP, the semiconductor substrate to be used for crystal growth is prepared by slice or grind to have a thickness of 400 μm or less, and the second surface 63b may be polished into a processed surface. With such a substrate thickness, breaking the substrate product provides, with a high yield, formation of the end facets that are flat and vertical enough to configure the laser cavity of the group III nitride semiconductor laser device. Breaking the substrate product can achieve formation of the end facets 67a and 67b free of ion damage. It is preferred that the second surface 63b be polished into a polished surface. It is also preferred that the thickness of the substrate product SP be equal to 50 μm or more for easy handling of the substrate product SP.

In the method for fabricating the laser end facets according to the present embodiment, the angle GAMMA described with reference to FIG. 2 is defined in the laser bar LB1 as well. In the laser bar LB1, the component (GAMMA)$_1$ of the angle GAMMA is preferably equal to or greater than (ALPHA −5) degrees and equal to or less than (ALPHA+5) degrees in a first plane (corresponding to the first plane S1 shown in FIG. 2) that is defined by the c-axis and m-axis of the group III nitride semiconductor. The end facets 67a and 67b of the laser bar LB1 satisfy the above-described verticality in terms of the angle component of the angle GAMMA defined in the direction from one of the c-axis and the m-axis to the other. The component (GAMMA)$_2$ of the angle GAMMA is preferably equal to or greater than −5 degrees and equal to or less than +5 degrees in a second plane (corresponding to the second plane S2 shown in FIG. 2). The end facets 67a and 67b of the laser bar LB1 satisfy the aforementioned verticality in terms of the angle component of the angle GAMMA defined in the plane perpendicular to the normal axis NX of the semipolar plane 51a.

Pressing the stack of plural gallium nitride based semiconductor layers, which are grown epitaxially on the semipolar plane 51a, breaks it into the new substrate product and laser bar, thereby forming the end facets 67a and 67b. Due to the epitaxial films on the semipolar plane 51a, the end facets 67a and 67b are not made of any of cleavage planes with low-plane indices, such as the c-plane, m-plane or a-plane that had conventionally been used as the cavity mirrors. However, breaking the stack of epitaxial films on the semipolar plane 51a allows the end facets 67a and 67b to have flatness and verticality applicable as the cavity mirrors.

The group III nitride semiconductor laser device according to the present embodiment uses the support base that has the c-axis thereof inclined therefrom toward the direction of the m-axis. This group III nitride semiconductor laser device, which has a laser waveguide extending along the plane defined by the c-axis and the m-axis, demonstrates a low threshold current. But, this direction of the waveguide disables the orientation of the laser cavity with cleavage planes.

According to the teaching of the inventors of the present invention, in the semiconductor device that uses the semipolar surface of the substrate in which the c-axis of the group III nitride is inclined therefrom toward the direction of the m-axis, the quality of the end facets can be adjusted for each individual direction of the <0001> axis (or <000-1> axis) through control of the method of fabricating them.

Regarding the control, the inventors have discovered that, for example, increasing the scanning speed of a laser beam for processing in forming the scribe grooves in the substrate product by the laser scriber can improve the verticality and smoothness of the scribe grooves with respect to the primary surface of the substrate product.

This type of control achieves production of the cavity mirrors that demonstrate lasing at a low threshold current. The cavity mirrors obtained by the method according to the present embodiment are composed of plural fractured planes different from the conventional cleavage planes, and thus are completely different from the conventional cavity mirrors. This semiconductor laser can eliminate the component of the returning light which may enter the laser diode though an end facet of the support base, and lessening the impact of the return light on the semiconductor laser.

Several prior arts show that a cavity mirror can be produced by means of dry etching technology such as a relative ion etching (RIE) method. The present embodiment, on the other hand, produces a cavity mirror by means of scribing and pressing. In production of cavity mirrors using the present method, in most cases, the quality of the end facets for the laser cavity is evaluated based on the observation of the appearances of the end facets, measurement/evaluation of the geometric angles, with or without the occurrence of lasing, magnitude of threshold current, and the like. For this reason, there is potential demand for an evaluation method that is suitable for finding the satisfactory fabrication conditions in terms of obtaining the verticality and flatness of the end facets. Regarding a group III nitride semiconductor laser device that uses end facets (fractured faces) as the cavity mirrors which are produced by pressing the substrate, a cavity mirror production method capable of providing more stable quality is desired, and an end facet evaluation method that is effective in finding such production recipes is also desired.

Example 1

A laser diode was grown by means of a metal organic vapor phase epitaxial method, as described below. Trimethylgallium (TMGa), trimethylaluminum (TMAl), trimethylindium (TMIn), ammonia ($NH_3$), silane ($SiH_4$), and bis(cyclopentadienyl)magnesium ($Cp_2Mg$) were used as the raw material. A {20-21} GaN substrate was prepared as a substrate 71. This GaN substrate can be produced by cutting a thick (0001) GaN ingot, grown by an HYPE method, with a wafer slicer at an angle of 75 degrees taken toward the direction of the m-axis.

Figure 6:
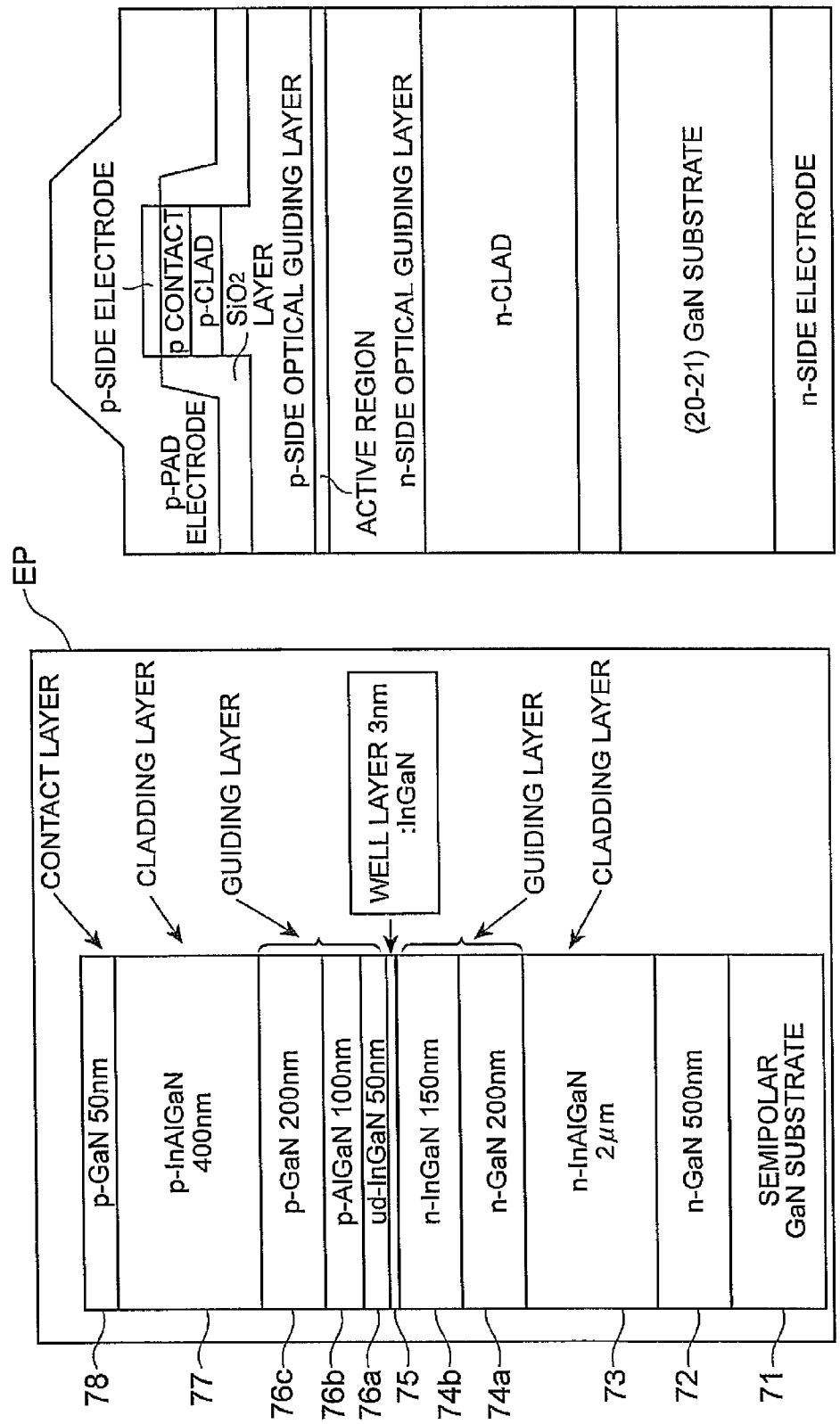
FIG. 6 is a view showing a laser structure and a structure of an epitaxial substrate according to an example.

After disposing this substrate on a susceptor in a reactor, epitaxial layers for a laser structure shown in FIG. 6 were grown by the following growth procedure. After disposing the substrate 71 in a reactor, first, an n-type GaN layer (thickness: 500 nm) 72 was grown on the substrate 71. Next, an n-type cladding layer (e.g., InAlGaN, thickness: 2000 nm) 73 was grown on the n-type GaN layer 72. Subsequently, a light emitting layer was grown thereon, and first, an n-type guiding layer (e.g., GaN, thickness: 200 nm) 74a and an n-type optical guiding layer (e.g., InGaN, thickness: 150 nm) 74b were grown on the n-type cladding layer 73; and next, an active layer 75 was grown thereon. This active layer 75 is configured by InGaN (a well layer, thickness: 3 nm) and GaN (a barrier layer, thickness: 15 nm), and has, for example, a 3-cycle multiple quantum well structure. Thereafter, an undoped optical guiding layer (e.g., InGaN, thickness: 50 nm) 76a, an electron blocking layer (e.g., p-type AlGaN, thickness 100 nm) 76b, and a p-type optical guiding layer (e.g., GaN, thickness 200 nm) 76e were grown on the active layer 75. Next, a p-type cladding layer (e.g., InAlGaN and/or AlGaN, thickness: 400 nm) 77 was grown on the light emitting layer. Finally, a p-type contact layer (e.g., GaN, thickness: 50 nm) 78 was grown on the p-type cladding layer 77. An epitaxial substrate EP is grown by growing these epitaxial layers.

A ridge structure is formed in this epitaxial substrate EP by means of a photolithography method and an etching method. For instance, in order to form a ridge structure with a width of 2 μm, a positive resist mask with a width of 2 μm is formed by means of photolithography. The direction of the laser waveguide was set to be parallel to a direction of the projection component defined by projecting the c-axis onto the primary surface. Chlorine gas ($Cl_2$), for example, was used in dry etching. Dry etching using $Cl_2$ creates the ridge structure.

The etching depth applied to produce the ridge structure is, for example, 0.7 µm, and, in the present example, the semiconductor region of the epitaxial substrate is etched until the AlGaN blocking layer is exposed. The resist mask was removed after the etching process. A stripe mask with a width of approximately 2 µm was left on the ridge structure by means of photolithography. The direction of the stripe mask was set to be in line with the direction of the ridge structure. Thereafter, $SiO_2$ was formed on a ridge sides by means of a vacuum deposition method. Subsequent to the deposition of the insulating film, a silicon oxide film (e.g., a $SiO_2$ film) on the ridge was removed by means of lift-off technology, and then an insulating film 79 with a stripe-shaped opening portion was formed. Next, an anode electrode and a cathode electrode were formed, resulting in producing a substrate product. Specifically, after the insulating film 79 was formed, a p-side electrode 80a and an n-side electrode 80b were produced to produce a substrate product. In order to form it, the p-side electrode 80a was produced by means of a vacuum deposition method. The p-side electrode 80a was made of, for example, Ni/Au. The rear surface of this epitaxial substrate is polished into a thickness of 80 µm. The rear surface was polished by using diamond slurry. The n-side electrode 80b was deposited on the polished surface. The n-side electrode 80b was made of Ti/Al/Ti/Au.

In order to produce a laser bar by scribing this substrate product, a laser scriber was used, which is capable of radiating a YAG laser of 355 nm wavelength, but the laser source is not limited to laser scribers. Scribe grooves were formed by radiating a laser beam directly onto the epi-surface through the insulating film of the substrate or the opening portion of the insulating film, at a pitch of 400 µm. The pitch of the scribe grooves corresponds to the width of the semiconductor laser devices and may be, for example, 400 µm. The scanning speed of the laser beam of the laser scriber is, for example, 5 mm/s, and the laser power is, for example, 100 mW. A blade was used to break the substrate product in order to produce cavity mirrors. The rear surface of the substrate product was pressed in order to produce a laser bar, thereby causing the substrate product to be broken. The pressing against the substrate product can be carried out using, for example, a breaking device. The blade indentation of the breaking device was, for example, 60 µm.

Thereafter, an end facet coating was applied thereto. A dielectric multilayer film with a combination of a silicon oxide film (e.g., $SiO_2$) and tantalum oxide film (e.g., $Ta_2O_5$) was used as the end facet coating. In the step of coating the end facets of the laser bar with dielectric multilayer films by means of a vapor deposition method, $SiO_2$ and $TiO_2$, for example, are stacked alternately to form each dielectric multilayer film. The thickness of each film is adjusted between 50 to 100 nm so that the central wavelength of the reflectivity of these films falls within the range of 500 to 530 nm.

Example 2

An experiment performed under the conditions for forming the scribe grooves in the epi-surface (e.g., the first surface) by means of the laser scriber will be described below. FIG. 7 is a diagram showing the formation of a scribe groove. The two cross-sectional shapes of the scribe grooves, which are formed under the respective conditions, are observed based on the cross sectional view taken along the m-n plane defined by the m-axis of the GaN substrate and the normal axis of the (20-21) plane. The following description illustrates the respective observation results of the shapes of the scribe grooves, which are formed under the above two types of conditions, shown in the cross section taken along the m-n plane defined by the normal axis and the m-axis of the support base. Part (a) of FIG. 7 shows the cross section of a scribe groove formed under condition A (laser beam output 33 mW; scanning speed 3 mm/s), where the depth of the groove is approximately 18 µm. Part (b) of FIG. 7 shows the cross section of a scribe groove formed under condition B (laser beam output 100 mW; scanning speed 11 mm/s), where the depth of the groove is approximately 24 µm. Part (a) of FIG. 7 shows that the bottom portion of the scribe groove is curved with respect to the normal axis of the epi-surface and accordingly has low perpendicularity. In the direction from the epi-surface towards the rear surface of the substrate, the scribe grooves changes its running direction to the −c axis of GaN of the substrate with respect to the normal axis of the epi-surface. The experiment by the inventors shows that the running direction constantly curves in the same direction without dependence on the scanning directions of scribing laser beams, and the changes in the running direction of the scribe grooves therefore are due to the crystal orientations. On the other hand, referring to the scribe groove shown in part (b) of FIG. 7, lowering of the perpendicularity in the depth direction in which the scribe groove extends is not observed. The inventors have discovered as follows: the above comparison reveals that the improvement of the perpendicularity of the scribe grooves with respect to the epi-surface and the improvement of the flatness of the formed end facets, are achievable by increasing the scanning speed of the laser beam in laser scribing.

The relationship between the scanning speed of the processing laser beam and the perpendicularity of the scribe grooves, which are formed under the following conditions: the laser beam outputs 33 mW; and 100 mW, is evaluated by the following method. First, an image of, for example, a scanning electron microscope (e.g., an SEM image) is prepared. On this SEM picture, a reference straight line or a reference line segment (reference line) is drawn in such a manner as to pass through both the position in the epi-surface of a scribe trace formed and the position in the bottom portion of the scribe trace formed. A normal line of the epi-surface is also drawn thereon, and the angle formed by the straight line and the normal line is measured. This angle provides a basis for evaluating the perpendicularity of each scribe groove with respect to the epi-surface. If necessary, the scribe grooves may be formed on the substrate rear surface, and the perpendicularity of the grooves with respect to the substrate rear surface can be evaluated in the same manner.

FIG. 8 is a diagram showing the relationship between the scanning speed of the processing laser beam and the curve pattern of each scribe groove. According to the result shown in part (b) of FIG. 8 and other experimental results provided by the inventors, the curve patterns of the scribe grooves are associated with the laser scanning speeds more strongly than to the output powers of the laser beam. The curve pattern of each scribe groove is defined by the angle formed by the reference line and the normal line, as shown in part (a) of FIG. 8. Referring to part (b) of FIG. 8, when the scanning speed of the processing laser beam is equal to or higher than 6 mm/s, the angle deviation shown in the longitudinal axis can be set substantially at 0 degrees. When the scanning speed of the processing laser beam is equal to or higher than 8 mm/s regardless of the output power of the laser beam, the angle deviation can stably be reduced to approximately 0 degrees. These results show that the scanning speed is preferably equal to or higher than 6 mm/s or more preferably equal to or higher than 8 mm/s. Moreover, the scanning speed of preferably 30 mm/s or less allows the stable formation of the arrangement of the scribe grooves spaced apart from each other.

The results shown in FIG. 8 may have the possibility of dependency on the model of the laser scriber used, and it is possible to obtain a relationship between the curve pattern of each scribe groove and the scanning speed of the processing laser beam from another laser scriber, and to determine, based on this relationship, a desired scanning speed of the processing laser beam. It is possible to obtain the relationship between the curve pattern of each scribe groove and the scanning speed of the processing laser beam and the output power of the laser beam, and to determine a desired scanning speed of the processing laser based on the relevant relationship.

Example 3

The respective scribe grooves are formed under conditions A and B, and thus created laser bars are evaluated (electrical current test) at room temperature. A pulsed power supply with a pulse width of 500 ns and a duty ratio of 0.1% is used as power sources. In the experiment, a probe metal needle is brought into contact with the electrode (anode) on the laser front surface, and the electrode on the rear surface of the laser bar (cathode electrode) is brought into contact with a metal stage. In this arrangement, the laser bar is fed with current. In the optical output measurement, the light emitted from the end facet of the laser bar is received by a photodiode to measure the photocurrent thereof. Based on this measurement, current-optical output characteristics (I-L characteristics) are examined, and the average value and standard deviation of the lasing threshold currents corresponding to the respective laser bars produced under condition A and condition B are shown below. Condition: number of lasing chips, average value (mA), standard deviation (mA).
Condition A: 191, 101.7, 37.1;
Condition B: 196, 82.2, 23.4.
These results show that the average value and standard deviation of the lasing threshold currents can be reduced by producing a laser bar under condition B. This is interpreted as that, under condition B, the improvement in the verticality and smoothness of the scribe grooves allows the quality of the cavity mirrors to become stable, thereby enhancing the laser production yield as well.

Example 4

The angles of the cavity mirrors of the produced laser bars are evaluated. This angle evaluation is carried out by a laser microscope. The laser microscope used in this example is equipped with an Ar-ion laser with a wavelength of 488 nm.

As schematically shown in part (a) of FIG. 9, each laser bar is tilted on a platform and then observed. In the present example, the laser bar is tilted at an angle of approximately 45 degrees. The first surface and the first processed end facet of the laser bar are relatively scanned with a laser beam across the edge at which the first surface meets the processed end facet of the laser bar, and the laser beam is run from either the processed end facet of the laser bar and the first surface toward the other. The processed end facet is evaluated using the reflected light of the laser beam used for the scanning. Based on the observation data obtained as a result of scanning with the laser beam, an image is created in the Z-X cross-section. In this Z-X cross-sectional view, the verticality of the cavity mirror is evaluated, with respect to the epi-surface or substrate rear surface, which is used as the reference plane.

Part (b) of FIG. 9 shows, as an observation example, the results of evaluating a laser bar created on a c-plane GaN substrate. This laser bar has a cavity mirror configured by the m-plane. The horizontal axis of part (b) of FIG. 9 represents the coordinates defined in the direction from either the processed end facet of the laser bar or the first surface of the laser bar to the other, and the direction is associated with the scanning direction of the laser beam. The longitudinal axis on the left-hand side represents the coordinates defined in a direction normal to a supporting plane of the platform, and the longitudinal axis on the right-hand side represents the angles of the processed end facet defined on the basis of the first surface of the laser bar. The longitudinal axis on the right-hand side of part (b) of FIG. 9 shows that the cavity mirror of this laser bar is formed substantially vertically on an axis from the epi-surface to the substrate rear surface.

Figure 10:
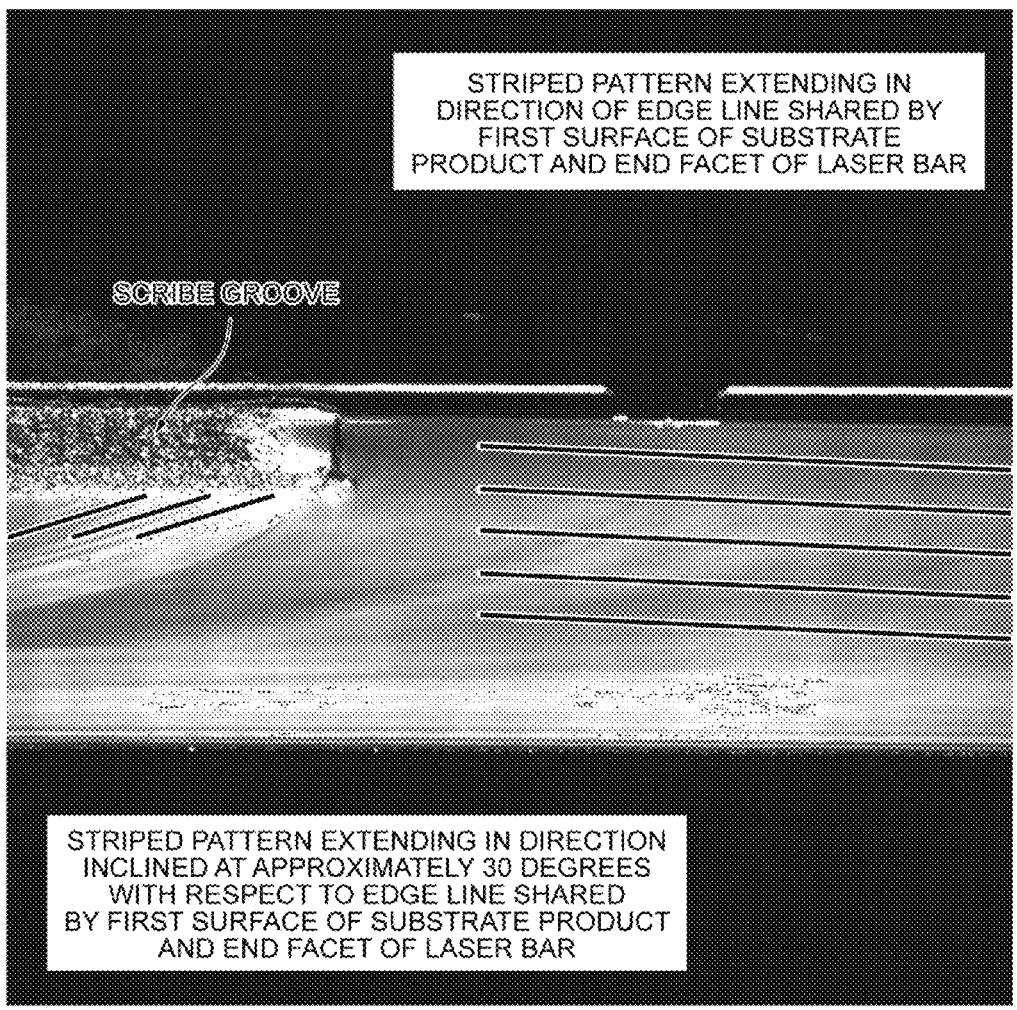
FIG. 10 is a view showing a laser microscope image of a mirror end facet for an optical cavity of a laser bar produced under a condition B.

Next, the cavity mirror of the laser bar produced under condition B is observed using this evaluation method. FIG. 10 shows an image of the end facet for the cavity mirror of the laser bar produced under condition B, where the image is obtained from the laser microscope. Referring to FIG. 10, streaky patterns are formed on the end facet below a scribe groove (on the support base side), in such a manner as to be inclined at approximately 30 degrees from the direction of the edge where the front surface (e.g., the epi-surface) of the device and the end facet of the laser bar meet. Also referring to FIG. 10, other streaky patterns are formed on another of the end facet where no scribe grooves are formed, in the direction of the edge where the front surface (e.g., the epi-surface) of the device and the end facet of the laser bar meet.

Next, FIG. 11 is a diagram showing the result of evaluation of the end facet (for the verticality) of the laser bar produced under condition B, where the evaluation result is obtained by the evaluation method described with reference to FIG. 9. The observation data in part (a) of FIG. 11, obtained with the laser microscope, are measured using the arrangement shown in part (b) of FIG. 11, and show the result of evaluation of the laser bar, based on the data of the laser microscope, which are obtained by the scanning along the m-n plane at a position corresponding to the laser waveguide (on the line passing on the laser beam emission area). As shown in FIG. 11, the angle of the end facet of the laser bar, defined with respect to the epi-surface as the reference plane in the m-n plane, is approximately 90 degrees at the position of the edge of the epi-surface, then monotonically drops in the direction from the epi-surface to the substrate rear surface, and becomes approximately 80 degrees at the position of the edge of the substrate rear surface.

In the manner described above, the verticality of the end facet of the laser bar can be evaluated by taking advantage of the laser beam scanning. The present example evaluates the end facets of the laser bar which is formed by pressing the substrate by means of the scribe grooves formed by the laser scriber. However, the end facets of the laser bar are not the only targets to be evaluated; thus, this evaluation method can be used for evaluating, for example, end facets for a laser cavity that are formed by means of dry etching. Attributes in the evaluation target are not limited to a specific plane orientation or an off-angle, and therefore the evaluation method can be used for evaluating end facets of the laser bar for optical cavity in relation to the impacts of the other factors such as the thickness of the substrate.

Example 5

Figure 12:
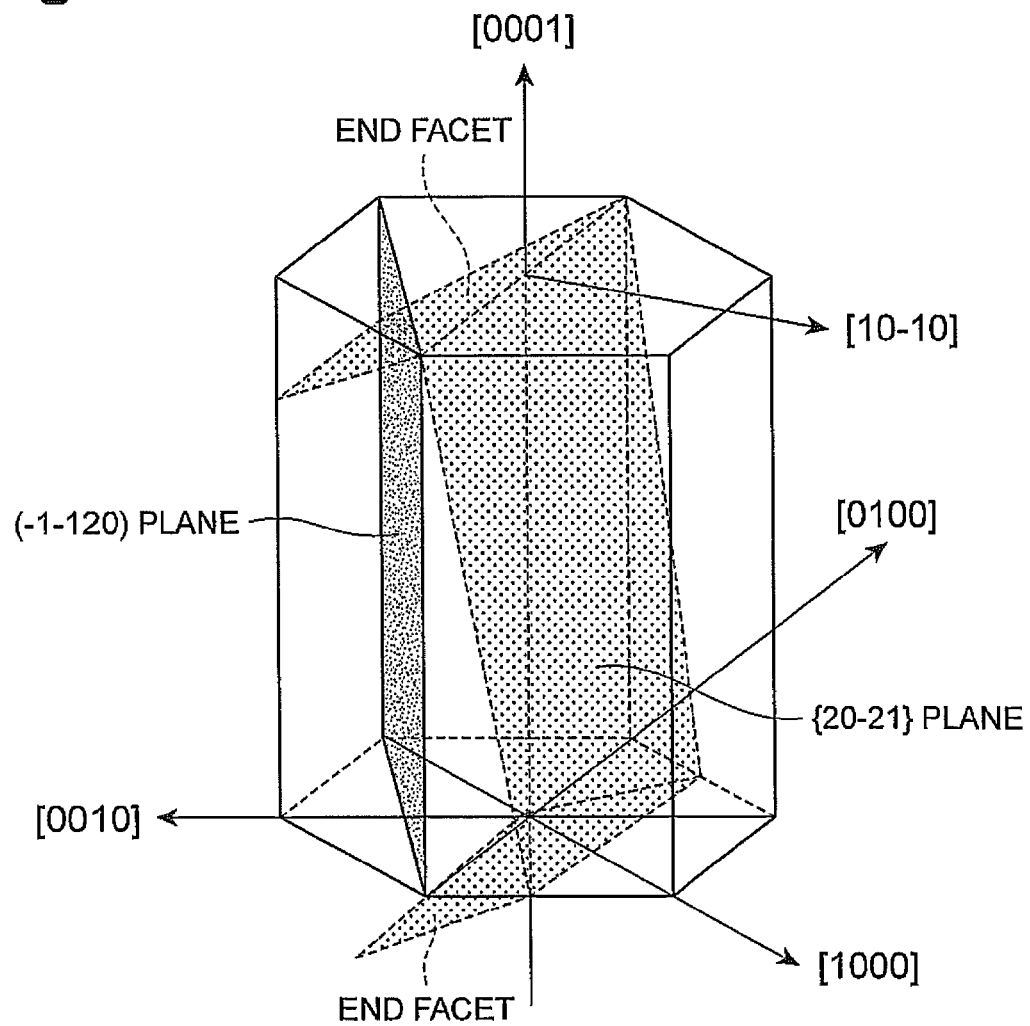
FIG. 12 is a view showing a hexagonal crystal lattice of a gallium nitride crystal structure.

The experimental result illustrated in Example 4 is considered based on a simple calculation using the crystal structure and lattice constant of group III nitride semiconductor. FIG. 12 shows a hexagonal crystal lattice having a gallium nitride crystal structure. Referring to FIG. 12, the streaky patterns on the end facet just below the scribe groove, illustrated in Example 4, can be considered as steps formed by the structure in which a (−1-120) plane of the support base meets the end facet of the laser bar.

Figure 13:
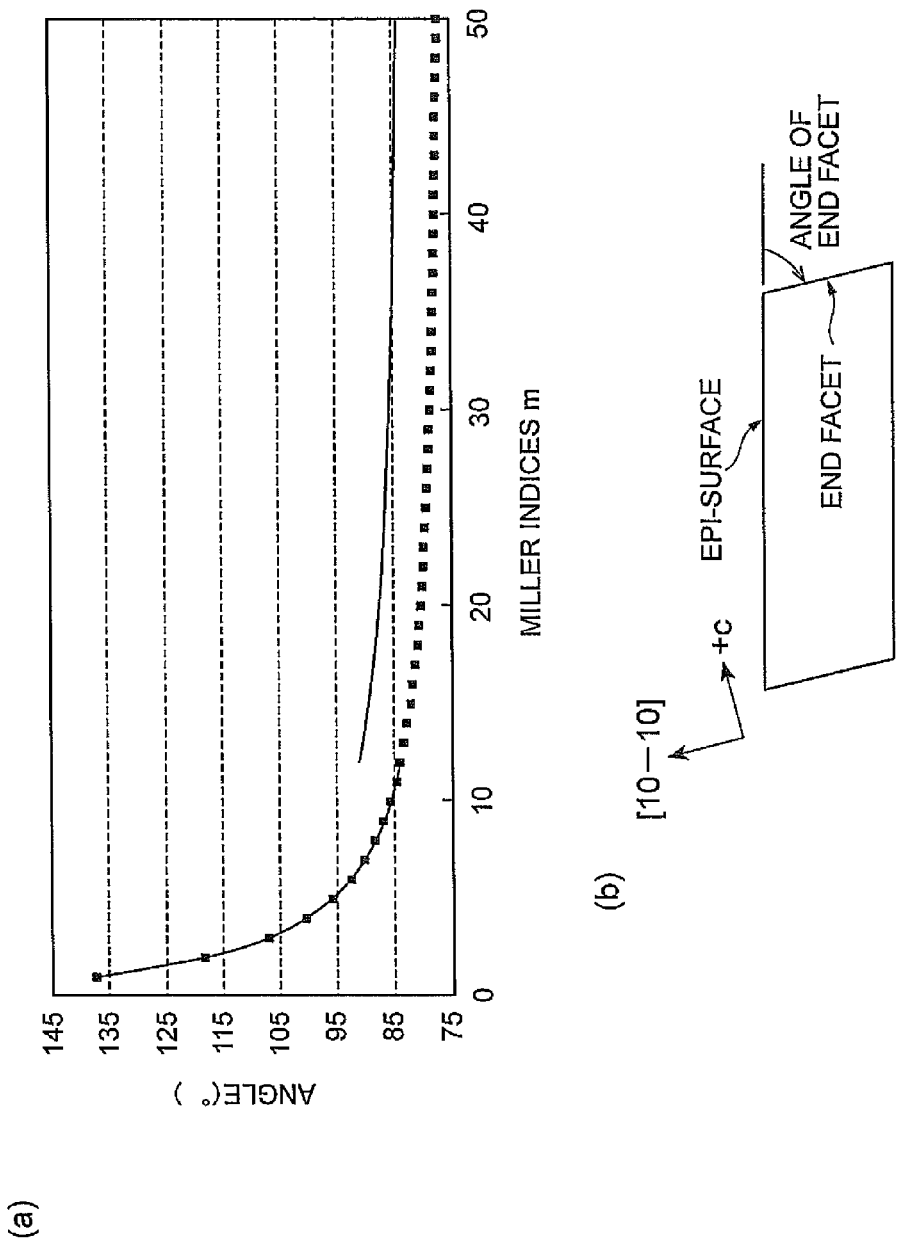
FIG. 13 is a list showing the computation of orientations (different from the orientation of an a-plane) that form angles approximate to 90 degrees with respect to a {20-21} plane of a GaN substrate for use in epitaxial growth.

Next, FIG. 13 shows a result of computing a list of plane orientations (different from the orientation of the a-plane) that form angles approximate to 90 degrees with the {20-21} plane of the GaN substrate on which the epitaxial layers are grown. Part (a) of FIG. 13 shows the angle formed by a (−101m) plane (where m=1, 2, . . . ) and the (20-21) plane, as a function of a Miller index m. In the plane orientation calculated in the arrangement shown in part (b) of FIG. 13, the c-plane of the GaN forms an angle of approximately 75.1 degrees with the (20-21) plane. Referring to FIG. 13, the streaky patterns that extend in the direction of the edge line where the epi-surface and the laser bar end facet meet, as illustrated in Example 4, are considered as steps that are formed by a structure where, for example, the (−101m) plane meets a (−101 (m+1)) plane. The steps each can be estimated to have a length of 20 nm or less because the observation data in the observation of the cross section using the laser microscope (see FIG. 9, for example) does not show no significant uneven structures on the end facet of the laser bar.

As a result of other experiments, the end facet obtained in the present example is estimated to form an angle of equal to or greater than 75 degrees but equal to or less than 80 degrees with the epi-surface, at the position of the edge line shared by the rear surface of the substrate and the end facet of the laser bar. In addition, the end facet of the laser bar obtained in the present example is estimated to form an angle of equal to or greater than 85 degrees but equal to or less than 100 degrees with the epi-surface at the position of the edge line shared by the epi-surface and the end facet of the laser bar.

In consideration of the fact that most of light returning to a semiconductor laser enters the waveguide of the laser semiconductor by reflection on the end facet of the support base, not on the end facet of the active layer, the end facet of the laser bar obtained in the present example contributes to lowering the impact of the return light in the nitride semiconductor laser because of the inclination of approximately 10 degrees with respect to the rear surface of the substrate, at the position of the rear surface of the substrate. Moreover, in the present example, because the laser bar end facet that satisfies the above-described angular quality can be formed by separating the laser bar from the substrate product once, the fabrication steps can be simplified, controlling the manufacturing cost accordingly.

Figure 14:
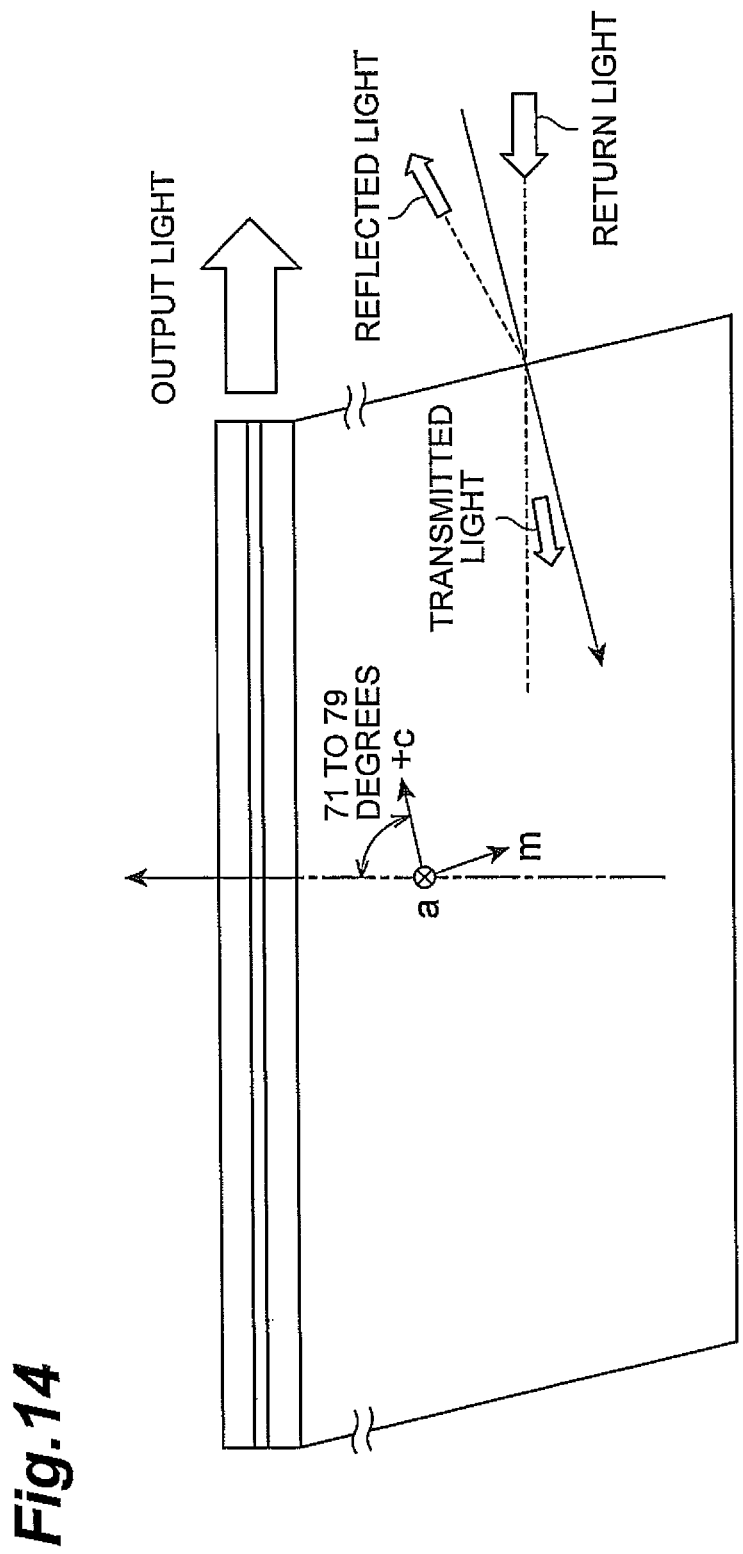
FIG. 14 is a view showing a diagrammatic representation in relation to laser return light.

FIG. 14 is a diagram schematically showing an arrangement of the planes in relation to laser return light. As shown in FIG. 14, when using the end facet of the laser bar on the +c axis vector side as a light emission surface, part of the return light propagating toward the support base of the semiconductor laser is reflected outward, whereas part of the return light entering the semiconductor laser propagates toward the rear surface of the substrate away from the optical waveguide due to optical refraction. The directions of the reflection and the refraction of the return light can prevent the return light from reaching the semiconductor region provided on the support base, and therefore the end facet structure according to the present embodiment can contribute to reduction of noise due to the return light.

Second Embodiment

Figure 15:
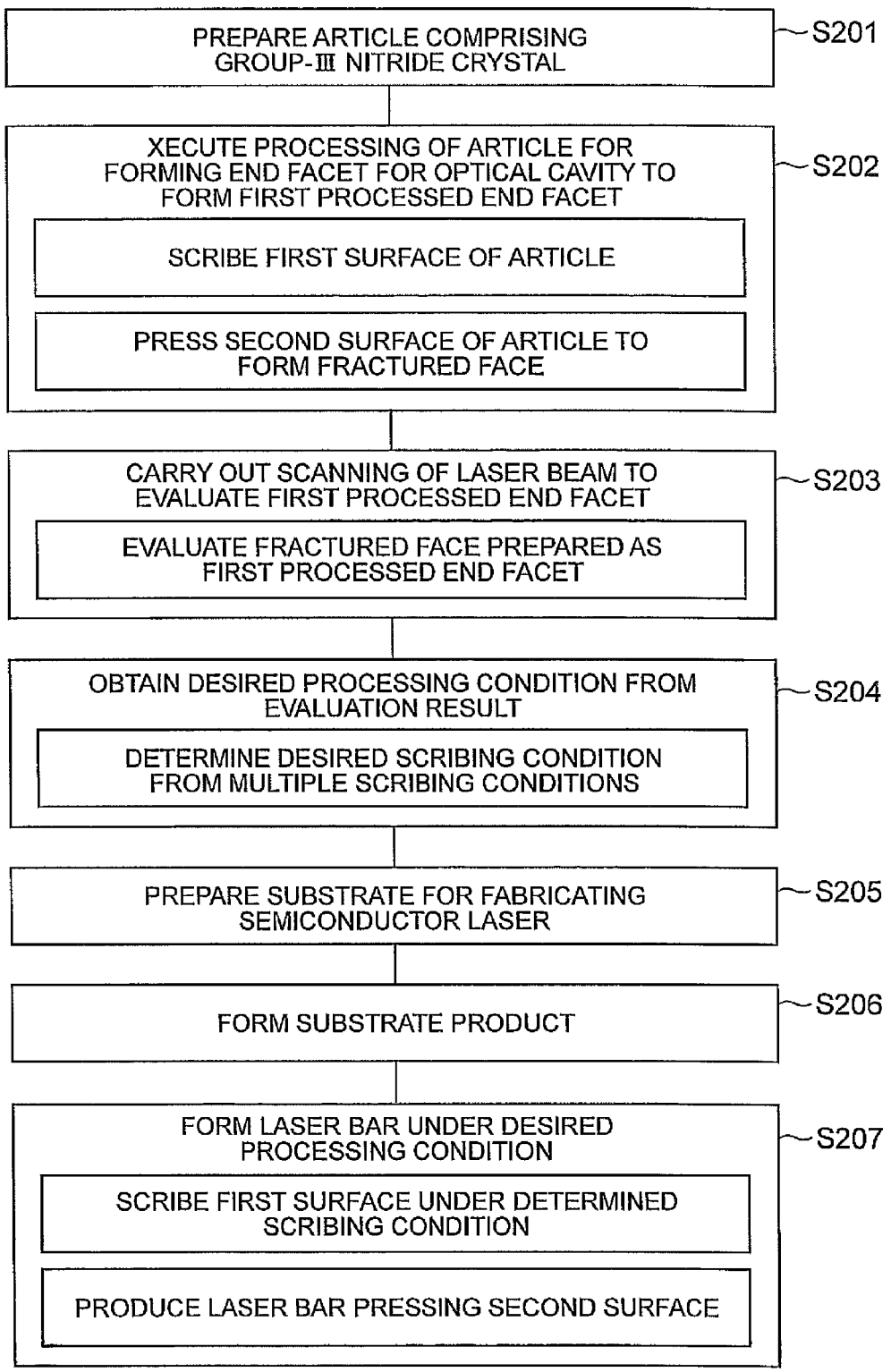
FIG. 15 is a schematic view showing primary steps of the method for producing the group III nitride semiconductor laser device according to the present embodiment.

FIG. 15 is a diagram showing primary steps of a method for producing a group III nitride semiconductor laser device according to the present embodiment.

In this production method, in step S201, one or more articles are prepared, and the articles contain group-III nitride crystal. Each article has a first surface and a second surface, and the second surface is on the opposite side of the first surface. In step S202, in order to form an end facet for an optical cavity of a group III nitride semiconductor laser device, each article is processed to form a first processed end facet extending from an edge of the first surface of the article. Plural processing conditions may be applied in order to form respective processed end facets. In each article the group III nitride semiconductor crystal is exposed on the processed end facet. In step S203, the first surface and the first processed end facet are relatively scanned with a laser beam, and the first processed end facet is evaluated using the reflected light component of the scanning laser beam. This scanning is performed in such a manner as to radiate the laser beam from either the first surface or the processed end facet to the other across the edge therebetween. The relative scanning can be carried out in the following manners: moving the laser source; moving the article; and moving both the laser source and the article. In the evaluation of the first processed end facet, processed end facet angles at a number of positions along the axial direction from either the first surface or the first processed end facet of the article to the other are evaluated from the reflected light, as illustrated in Example 4. The processed end facet angles are each defined as an angle formed by a tangential plane, which is defined at each of the positions on the first processed end facet, with the reference plane extending along the first surface. In step S204, a desired processing condition is obtained from the results of evaluation under the plural conditions. The evaluation of the end facet is carried out through the above steps. This evaluation method is not limited to evaluate the end facets for the cavity that are produced by forming the scribe grooves and then breaking the substrate by pressing.

Subsequently, in step S205, a substrate is prepared for producing semiconductor laser. This substrate may have a primary surface made of the group III nitride semiconductor. In step S206, a substrate product is prepared. This substrate product includes a substrate, a semiconductor region grown on the primary surface of the substrate, and an electrode. This preparation is accomplished by producing, for example, the substrate product described in the above examples. In step S207, the substrate product is processed using the desired processing condition to form another substrate product and a laser bar from the substrate product. This laser bar includes a first end facet formed by the processing step, and the laser cavity of the group III nitride semiconductor laser device includes the first end facet.

In the method for producing the group III nitride semiconductor laser device, the process for forming an end facet for the optical cavity is applied to an article (e.g., a physical object) under plural processing conditions, to form the first processed end facet described above, and then the first surface and the first processed end facet are relatively scanned with a laser beam as described above, to evaluate the first processed end facet by using the reflected light of the laser beam. In this evaluation, the reflected light of the laser beam is used to provide the inclination angle that are formed by the first processed end facet with the first surface (i.e., the verticality of the first processed end facet). The evaluation result is used to determine a desired processing condition from the plural processing conditions. The process under the desired processing condition is applied to the substrate product to produce another substrate product and a laser bar therefrom. This method can demonstrate the character distribution located around a desired quality. This contributes to the improvement of the yield.

In, a favorable embodiment, the step of forming the first processed end facet (in step S202) performs scribing the first surfaces of the articles under respective scribing conditions in step S202-1. After scribing the first surface of each article, the second surface of the article is pressed in step S202-2 to form a fractured end facet, which extends in the direction from the first surface of the article to the second surface. The step of evaluating the first processed end facet (in step S203) performs evaluates a first fractured face prepared as the first processed end facet in step S203-1. The first and second fractured faces in this example each extend from the first surface of the laser bar to the second surface thereof. Furthermore, the step of selecting one processing condition (in step S204) performs determining a desired scribing condition from the plural scribing conditions in step S204-1. The step of forming another substrate product and a laser bar (in step S207) performs, in step S207-1, scribing the first surface of the substrate product using the determined scribing condition, and in step S207-2, pressing the second surface of the substrate product to separate the substrate product to form another substrate product and laser bar.

In this production method, after processing to form an end facet for an optical cavity is applied to the articles (e.g., sample) under the respective scribing conditions to form the above first processed end facet in each article, the first surface and the first processed end facet in the article are relatively scanned with a laser beam to evaluate the first processed end facet using the reflected light of the laser beam, as described above. According to this evaluation, the trend in the changing angle of the first processed end facet with respect to the first surface (i.e., the verticality of the first processed end facet) can be derived from the reflected light of the laser beam. The evaluation results from the plural scribing conditions are used to find a desired scribing condition. The substrate product is processed under the desired processing condition to produce another substrate product and laser bar from the substrate product. The above method allows the distribution of characteristics in the fabricating method to lie around a quality close to a desired quality of the product. This contributes to the improvement in the yield.

It is preferred that a laser microscope be employed for the laser beam scanning. The laser microscope facilitates the evaluation of end facets for the optical cavity. A laser scriber can be used as the scriber. The laser scriber can facilitate the control of the scribing process. The scribing conditions may include the scanning speed and laser power in the laser scriber. Adjusting the scanning speed is effective in controlling the scribing associated with the present method.

Physical objects to which the evaluation of the end facets is applicable include the substrate with the primary surface that is inclined with respect to the reference plane perpendicular to the c-axis of the group III nitride semiconductor of the substrate. The present embodiment is applied to an aspect where the primary surface of the substrate is inclined with respect to the reference plane perpendicular to the c-axis of the group III nitride semiconductor of the substrate.

Physical objects to which the evaluation of the end facets is applicable include the substrate with the primary surface that is inclined with respect to the reference plane perpendicular to the a-axis of the group III nitride semiconductor of the substrate. The present embodiment is applied to an aspect where the primary surface of the substrate is inclined with respect to the reference plane perpendicular to the a-axis of the group III nitride semiconductor of the substrate.

Physical objects to which the evaluation of the end facets is applicable include the substrate with the primary surface that is inclined with respect to the reference plane perpendicular to the m-axis of the group III nitride semiconductor of the substrate. The present embodiment is applied to an aspect where the primary surface of the substrate is inclined with respect to the reference plane perpendicular to the m-axis of the group III nitride semiconductor of the substrate.

Physical objects to which the evaluation of the end facets is applicable include a substrate with a semipolar primary surface made of a group III nitride semiconductor. The first cladding layer, the second cladding layer, and the active layer are epitaxially grown on this semipolar plane so as to be arranged along the direction of the normal component of the +c axis vector, and extend in the direction of the parallel component of the +c axis vector to form a laser waveguide structure extending on the semipolar primary surface. This production method allows the crystal axis of the semiconductor region to be associated with the crystal axis of the support base because the first cladding layer, the second cladding layer, and the active layer are epitaxially grown on the semipolar primary surface and arranged along the direction of the normal component of the c-axis vector VC. In the formation of the end facets, the association between the +c axis vector directions of the semiconductor region and the support base is kept.

The evaluation method described above can be applied to an aspect where the c-axis of the group III nitride semiconductor of the substrate is inclined with respect to the normal axis of the substrate primary surface therefrom toward the direction of the m-axis of the group III nitride semiconductor so that the first and second end facets intersect with the m-n plane. The evaluation method can also be applied to an aspect where the c-axis of the group III nitride semiconductor of the substrate is inclined with respect to the normal axis therefrom toward the direction of the a-axis of the group III nitride semiconductor so that the first and second end facets intersect with the a-n plane defined by the a-axis of the group III nitride semiconductor and the normal axis of the substrate primary surface. Here, the a-n plane is perpendicular to the m-n plane.

The evaluation method can also be applied to an aspect where the primary surface of the substrate with extends along the reference plane parallel to the plane orientation of the c-plane, the a-plane or the m-plane of the group III nitride semiconductor of the substrate. The above production method can be applied to an aspect where the primary surface of the substrate extends along the reference plane parallel to the plane orientation of the c-plane, the a-plane or the m-plane of the group III nitride semiconductor of the substrate.

Physical objects to which the evaluation of the end facets is applicable include a group-III nitride substrate, and the group-III nitride substrate may have a thickness of equal to or less than 400 μm. The processing conditions may include the use of substrates having different thicknesses. The thickness of the group-III nitride substrates can be, for example, equal to or greater than 50 μm but equal to or less than 100 μm. The above method can be used for not only the evaluation of the processing conditions for the end facet but also the relationship between the structure of the laser structure and the end facets thereof.

Figure 16:
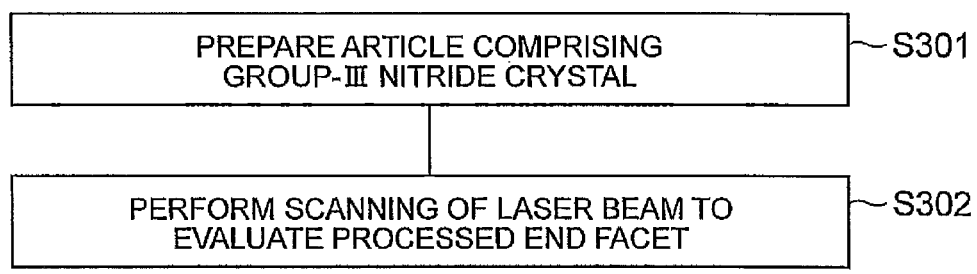
FIG. 16 is a schematic view showing primary steps of a method for evaluating an end facet for an optical cavity of the group III nitride semiconductor laser device according to the present embodiment.

FIG. 16 is a diagram showing main steps of the method for evaluating an end facet for the optical cavity of a group III nitride semiconductor laser device according to the present embodiment. The plane orientations of the substrate in the description of the production method, illustrated with reference to FIG. 15, are applied to the present embodiment as well.

In the method for evaluating an end facet shown in FIG. 16, in step S301, an article is prepared which includes a hexagonal group III nitride semiconductor crystal. This article has a processed end facet for an optical cavity, which is formed under a processing condition, of a group III nitride semiconductor laser device; a first surface; and a second surface disposed on opposite side of the first surface. The processed end facet extends along a plane intersecting with the first surface and the second surface. The group III nitride semiconductor crystal is exposed on the processed end facet. In step S302, the first surface and the processed end facet are scanned with a laser beam in the axial direction from the first surface or processed end facet of the article to the other, to evaluate the processed end facet across the edge therebetween, thereby obtaining the reflected light of the scanning laser beam. In this evaluation, the trend of the changing angle of the processed end facet measured along the axial direction is obtained from the light reflected thereby, and the changing angle of the processed end facet is defined as an angle that is formed by a tangential plane of the processed end facet with the reference plane extending along the first surface. The evaluation method can provide results from evaluation of the processed end facet in relation to the structure of the article and/or the processing condition.

Figure 17:
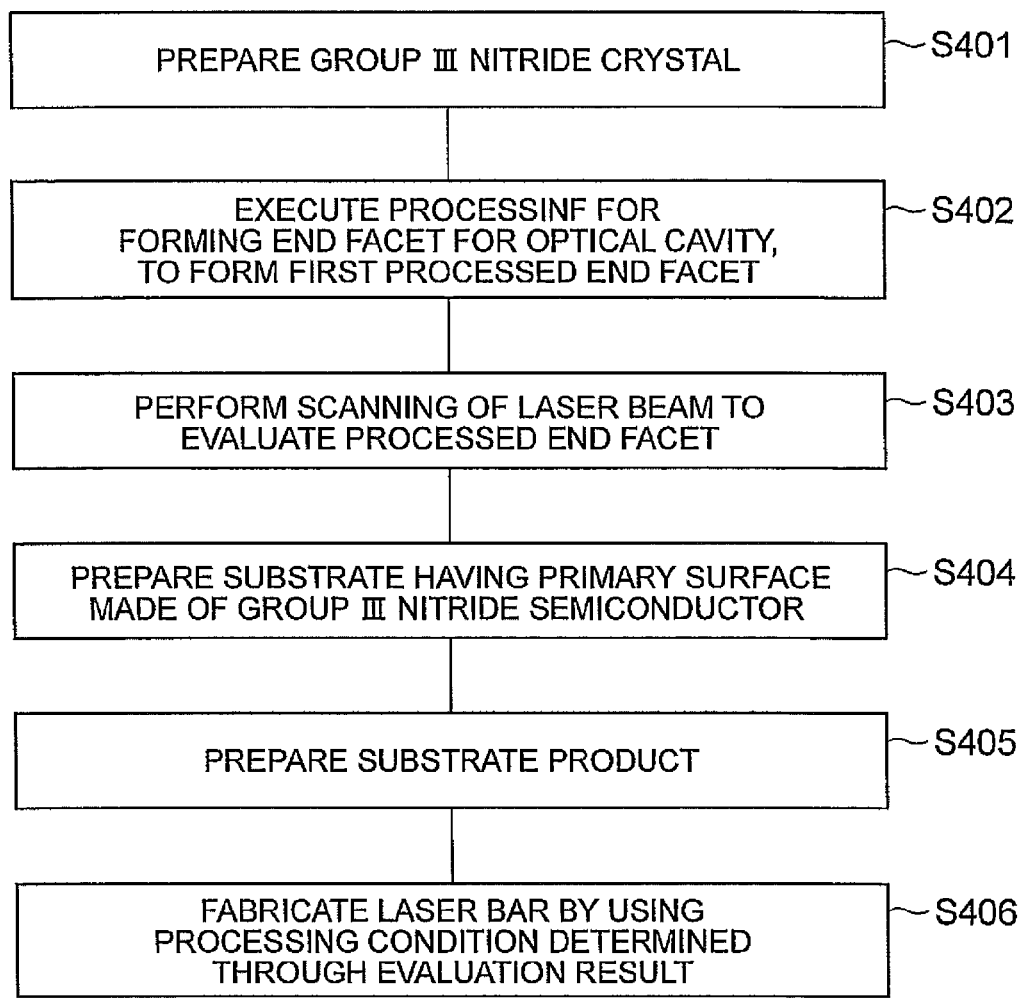
FIG. 17 is a schematic view showing primary steps of the method for evaluating an end facet for the optical cavity of a group III nitride semiconductor laser device according to the present embodiment.

FIG. 17 is a diagram showing main steps of the method for evaluating an end facet for the optical cavity of a group III nitride semiconductor laser device according to the present embodiment. The plane orientations of the substrate in the description of the production method, illustrated with reference to FIG. 15, are applied to the present embodiment as well.

In the end facet evaluation method shown in FIG. 17, in step S401, an article is prepared which includes a hexagonal group III nitride semiconductor crystal. This article has a first surface and a second surface, and the second surface is on opposite side of the first surface. In step S402, a processing of the article is carried out under a certain processing condition, the processing of the article is used for forming an end facet for the optical cavity of a group III nitride semiconductor laser device and forms a first processed end facet extending from the edge of the first surface. In step S403, the first surface and the processed end facet are scanned with a laser beam along the axial direction from the first surface or the processed end facet of the article to the other across the edge therebetween, to evaluate the processed end facet by using the reflected light of the scanning laser beam. In this evaluation, the angle of the processed end facet along the axial direction is obtained from the reflected light, and this processed end facet angle is defined as an angle formed by the processed end facet with the reference plane extending along the first surface.

According to this evaluation method, the process to form an end facet for the optical cavity is performed on articles (e.g., a sample) under respective processing conditions, to form a first processed end facet in each article, and thereafter, the first surface and the first processed end facet are relatively scanned with a laser beam, to evaluate the first processed end facet by using the reflected light of the laser beam, as described above. According to this evaluation, the inclination angle of the first processed end facet with respect to the first surface (i.e., the verticality of the first processed end facet) can be obtained from the reflected light of the laser beam. This evaluation method allows the examination of the quality of the end facet in relation to the processing conditions.

If needed, in step S404, a substrate is prepared which has a primary surface made of a group III nitride semiconductor. In step S405, a substrate product is prepared which has a semiconductor region grown on the substrate primary surface; a substrate; and an electrode. In step S406, after the evaluation, a processing of the substrate product is carried out by using a desired processing condition determined based on the processing conditions, to form another substrate product and laser bar from the substrate product. This laser bar has a first end facet formed through the above processing. The laser cavity of the group III nitride semiconductor laser device includes the first end facet.

In the evaluation method described above, after the quality of the end facet is examined in relation to the processing condition, the processing can be applied to the substrate product by using a desired processing condition determined based on the processing conditions, to form another substrate product and laser bar from the substrate product. According to this evaluation method, a distribution in accordance with the desired quality can be obtained in the manufacture of the group III nitride semiconductor laser device. The use of this evaluation method can achieve an improvement of the production yield.

Figure 18:
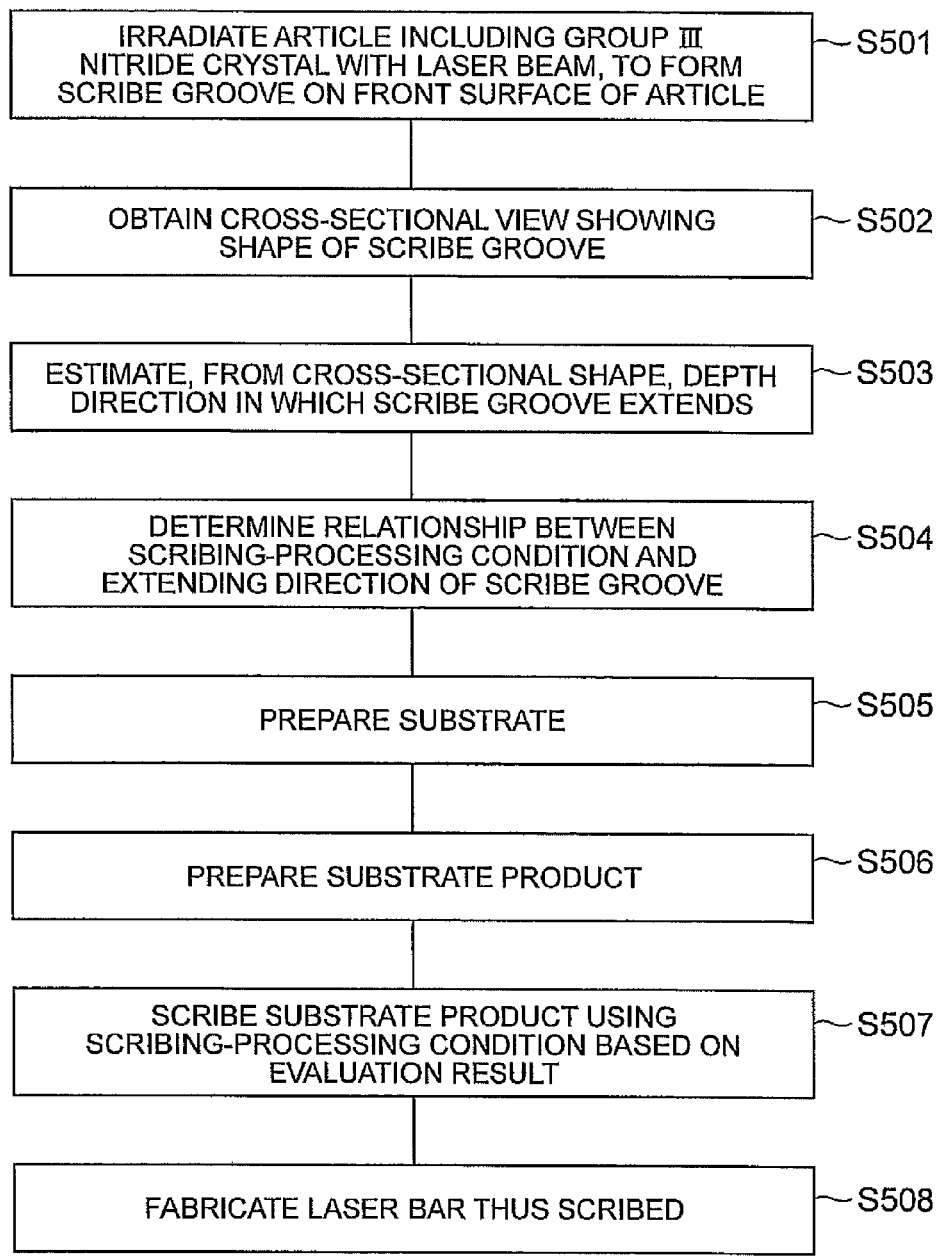
FIG. 18 is a schematic view showing primary steps of a method for evaluating a scribe groove for the optical cavity of a group III nitride semiconductor laser device according to the present embodiment.

FIG. 18 is a diagram showing main steps of a method for evaluating a scribe groove for an optical cavity of a group III nitride semiconductor laser device according to the present embodiment. The plane orientations for the substrate in the description for the production method illustrated with reference to FIG. 15, are also applied to the present embodiment as well.

In the end facet evaluation method shown in FIG. 18, in step S501, a laser beam is radiated onto the front surfaces of articles, each of which includes a hexagonal group III nitride semiconductor crystal, under the scribing-processing conditions for an optical cavity of a group III nitride semiconductor laser device, and thereby forms a scribe groove on the front surface in each article. In step S502, a cross-sectional shape of the scribe groove is observed. In step S503, the depth direction in which the scribe groove extends is estimated from the shape shown in the cross-sectional view obtained by the observation (e.g., observation using an SEM or an optical microscope). In step S504, the relationship between the scribing-processing condition and the direction in which the scribe groove extends in depth is determined based on the result of the estimate.

In this evaluation method, if necessary, in step S505 a substrate is prepared which has a primary surface made of the group III nitride semiconductor. In step S506, a substrate product is prepared which has a semiconductor region grown on the substrate primary surface; a substrate; and an electrode. In step S507, a scribe groove is formed in the substrate product by using a desired scribing-processing condition determined based on the scribe processing conditions. After the scribe groove is formed, the aforementioned substrate product is pressed in step S508 to form another substrate product and laser bar. This laser bar has a first end facet formed through the processing described above. The laser cavity of this group III nitride semiconductor laser device includes the first end facet.

The present invention is not limited to the specific configurations disclosed in these embodiments.

INDUSTRIAL APPLICABILITY

As described above, these embodiments provide a group III nitride semiconductor laser that has a laser cavity capable of reducing disturbance caused by return light, on a semipolar plane of a substrate in which a c-axis of group-III nitride is inclined in the direction of an m-axis. In addition, the present invention provides a method for producing this group III nitride semiconductor laser.

The above embodiments provide a method for producing a group III nitride semiconductor laser device, which is capable of adjusting the quality of an end facet that emits, reflects, and/or transmits a laser beam. In addition, the above embodiments provide a method for evaluating an end facet for the optical cavity of the group III nitride semiconductor laser device.

The above embodiments also provide a method for evaluating a scribe groove used for forming the optical cavity end facet of the group III nitride semiconductor laser device.

REFERENCE SIGNS LIST

11 . . . Group III nitride semiconductor laser device;
13 . . . Laser structure;
13a . . . First surface;
13b . . . Second surface;
13c, 13d . . . Edge;
15 . . . Electrode;
17 . . . Support base;
17a . . . Semipolar primary surface;
17b . . . Support base rear surface;
17c . . . Support base end facet;
19 . . . Semiconductor region;
19a . . . Semiconductor region front surface;
19c . . . Semiconductor region end facet;
21 . . . First cladding layer;
23 . . . Second cladding layer;
25 . . . Active layer;
25a . . . Well layer;
25b . . . Barrier layer;
27, 29 . . . End facet;
ALPHA . . . Angle;
Sc . . . C-plane;
NX . . . Normal axis;
31 . . . Insulating film;
31a . . . Insulating film opening;
35 . . . n-side optical guiding layer;
37 . . . p-side optical guiding layer;
39 . . . Carrier blocking layer;
41 . . . Electrode;
43a, 43b . . . Dielectric multilayer film;
MA . . . M-axis vector;
GAMMA . . . Angle;
51 . . . Substrate;
51a . . . Semipolar primary surface;
SP . . . Substrate product;
57 . . . Gallium nitride based semiconductor region;
59 . . . Light emitting layer;
61 . . . Gallium nitride based semiconductor region;
53 . . . Semiconductor region;
54 . . . Insulating film;
54a . . . Insulating film opening;
55 . . . Laser structure;
58a . . . Anode electrode;
58b, Cathode electrode;
63a . . . First surface;
63b . . . Second surface;
10a . . . Laser scriber;
65a . . . Scribe groove;
65b . . . Scribe groove;
LB . . . Laser beam;
SP1 . . . Substrate product;
LB1 . . . Laser bar;
69 . . . Blade;
69a . . . Edge;
69b, 69c . . . Blade surface;
71 . . . Support device;
71a . . . Supporting surface;
71b . . . Recess portion.

The invention claimed is:

1. A group III nitride semiconductor laser device, comprising:
a laser structure including a support base and a semiconductor region, the support base being made of a hexagonal group III nitride semiconductor and having a semipolar primary surface, and the semiconductor region being provided on the semipolar primary surface of the support base; and
an electrode provided on the semiconductor region of the laser structure,
a c-axis of the group III nitride semiconductor of the support base being oriented in a direction of a <0001> axis of the group III nitride semiconductor,
the direction of the <0001> axis being indicated by a +c axis vector,
the semiconductor region including an active layer, and the active layer including a gallium nitride based semiconductor layer,
the c-axis of the group III nitride semiconductor of the support base forming an angle ALPHA with a normal axis normal to the semipolar primary surface in a direction away from the c-axis toward a [−1010] axis of the group III nitride semiconductor, the angle ALPHA being equal to or greater than 71 degrees but equal to or less than 79 degrees,
the laser structure including a first end facet and a second end facet, the first end facet and the second end facet intersecting with an m-n plane defined by the normal axis and an m-axis of the group III nitride semiconductor, and a laser cavity of the group III nitride semiconductor laser device including the first end facet and the second end facet,
the laser structure including a first surface and a second surface, the first surface being provided on opposite side of the second surface, the semiconductor region being provided between the first surface and the support base,
a first normal vector normal to the first end facet being defined at a first edge shared by the first end facet and the first surface, and the +c axis vector being inclined at an angle α1 with respect to the first normal vector within the m-n plane in a direction away from the [−1010] axis toward the c-axis, the angle α1 being equal to or greater than 10 degrees but equal to or less than 25 degrees,
a second normal vector normal to the first end facet being defined at a second edge shared by the first end facet and the second surface, and the +c axis vector being inclined at an angle β1 with respect to the second normal vector within the m-n plane in the direction from the [−1010] axis toward the c-axis, the angle β1 being equal to or greater than zero degrees but equal to or less than 5 degrees, and
an end facet of the support base and an end facet of the semiconductor region being exposed on each of the first end facet and the second end facet.

2. A group III nitride semiconductor laser device, comprising:
a laser structure including a support base and a semiconductor region, the support base being made of a hexagonal group III nitride semiconductor and including a semipolar primary surface, and the semiconductor region being provided on the semipolar primary surface of the support base; and an electrode provided on the semiconductor region of the laser structure, a c-axis of the group III nitride semiconductor of the support base being oriented in a direction of a <0001> axis of the group III nitride semiconductor, the direction of the <0001> axis being indicated by a +c axis vector, the semiconductor region including an active layer, and the active layer including a gallium nitride based semiconductor layer, the c-axis of the group III nitride semiconductor of the support base forming an angle ALPHA with a normal axis normal to the semipolar primary surface in a direction away from the c-axis toward a [−1010] axis of the group III nitride semiconductor, the angle ALPHA being equal to or greater than 71 degrees but equal to or less than 79 degrees, the laser structure including a first end facet and a second end facet, the first end facet and the second end facet intersecting with an m-n plane defined by the normal axis and an m-axis of the group III nitride semiconductor, and a laser cavity of the group III nitride semiconductor laser device including the first end facet and the second end facet, the laser structure including a first surface and a second surface, the first surface being provided on opposite side of the second surface, the semiconductor region being provided between the first surface and the support base, a first normal vector normal to the first end facet being defined at a first edge shared by the first end facet and the first surface, and the +c axis vector being inclined at an angle α1 with respect to the first normal vector within the m-n plane in a direction away from the [−1010] axis to the c-axis, a second normal vector normal to the first end facet being defined at a second edge shared by the first end facet and the second surface, and the +c axis vector being inclined at an angle β1 with respect to the second normal vector within the m-n plane in the direction from the [−1010] axis toward the c-axis, the angles α1 being different from the angle β1, the angles α1 and the angle β1 having the same sign, and an absolute value of the angle α1 being greater than that of the angle β1, the first end facet having a streaky structure, the streaky structure including streaks extending in a direction of an cross product of the c-axis and the m-axis, and each of the first end facet and the second end facet including an end facet of the support base and an end facet of the semiconductor region.

3. The group III nitride semiconductor laser device according to claim 1, wherein the +c axis vector includes a normal component in a direction of the normal axis of the semipolar primary surface, and a parallel component in a direction parallel to the semipolar primary surface, wherein the laser structure includes a laser waveguide structure extending on the semipolar primary surface of the support base, and wherein the parallel component of the +c axis vector is in a direction from the second end facet toward the first end facet, and the laser waveguide structure extends in a direction of the parallel component of the +c axis vector.

4. The group III nitride semiconductor laser device according to claim 1, wherein the +c axis vector includes a normal component in a direction of the normal axis of the semipolar primary surface, and a parallel component in a direction parallel to the semipolar primary surface, wherein the semiconductor region includes a first cladding layer made of a group III nitride semiconductor of a first conductivity type and a second cladding layer made of a group III nitride semiconductor of a second conductivity type, and the active layer is provided between the first cladding layer and the second cladding layer, wherein the first cladding layer, the second cladding layer, and the active layer are epitaxially grown on the semipolar primary surface and arranged along a direction of the normal component of the +c axis vector, and the first cladding layer, the second cladding layer, and the active layer extend in a direction of the parallel component of the +c axis vector and compose a laser waveguide structure extending on the semipolar primary surface of the support base.

5. The group III nitride semiconductor laser device according to claim 1, wherein the c-axis of the group III nitride semiconductor of the support base extends in a direction opposite to a direction of a <000-1> axis of the group III nitride semiconductor, wherein the direction of the <000-1> axis is represented as a −c axis vector, wherein a third normal vector normal to the second end facet is defined at a third edge shared by the second end facet and the first surface, the −c axis vector is inclined at an angle α2 with respect to the third normal vector within the m-n plane in a direction away from the [−1010] axis toward the c-axis, and the angle α2 is +10 degrees to +25 degrees, wherein a fourth normal vector normal to the second end facet is defined at a fourth edge shared by the second end facet and the second surface, the −c axis vector is inclined at an angle β2 with respect to the fourth normal vector within the m-n plane in the direction away from the [−1010] axis toward the c-axis, and the angle β2 is 0 degrees to +5 degrees, and wherein the first end facet and the second end facet are provided to form in such a manner that the first end facet is configured as a light emission face.

6. The group III nitride semiconductor laser device according to claim 1, wherein the support base has a thickness of 100 μm or less.

7. The group III nitride semiconductor laser device according to claim 1, wherein a laser beam from the active layer is polarized in a direction of an a-axis of the group III nitride semiconductor.

8. The group III nitride semiconductor laser device according to claim 1, wherein light in an LED-mode of the group III nitride semiconductor laser device includes a polarization component I1 in a direction of the a-axis of the group III nitride semiconductor and a polarization component I2 in a direction of the c-axis projected onto the primary surface, and wherein the polarization component I1 is larger than the polarization component I2.

9. The group III nitride semiconductor laser device according to claim 1, wherein the semipolar primary surface falls within a range of −4 degrees to +4 degrees with respect to a {20-21} plane.

10. The group III nitride semiconductor laser device according to claim 1, wherein the semipolar primary surface includes a {20-21} plane.

11. The group III nitride semiconductor laser device according to claim 1, wherein the support base has a stacking fault density of $1 \times 10^4$ cm$^{-1}$ or lower.

12. The group III nitride semiconductor laser device according to claim 1, wherein the support base comprises one of GaN, AlGaN, AlN, InGaN, and InAlGaN.

13. The group III nitride semiconductor laser device according to claim 1, further comprising a dielectric multi-layer film provided on at least one of the first end facet or the second end facet.

14. The group III nitride semiconductor laser device according to claim 1, wherein the active layer includes a light emitting region generating light of a wavelength of equal to or greater than 360 nm but equal to or less than 600 nm.

15. The group III nitride semiconductor laser device according to claim 1, wherein the active layer includes a quantum well structure generating light of a wavelength of equal to or greater than 430 nm but equal to or less than 550 nm.

16. The group III nitride semiconductor laser device according to claim 1,
wherein each of the first end facet and the second end facet extends from the first edge of the first surface to the second edge of the second surface, and
wherein an angle formed by an end facet of the active layer of the semiconductor region with a reference plane perpendicular to an m-axis of a support base of the nitride semiconductor is equal to or greater than −5 degrees but equal to or less than +5 degrees in a second plane, and the second plane is perpendicular to the normal axis and a first plane defined by the c-axis and m-axis of the group III nitride semiconductor.

17. The group III nitride semiconductor laser device according to claim 1, further comprising an insulating film provided on the semiconductor region, the group III nitride semiconductor laser device having a gain waveguide structure,
wherein the electrode is in contact with the semiconductor region via an opening of the insulating film, and
wherein the angle α1 and the angle β1 are defined on an axis located at a center of a width of the opening of the insulating film, the axis extends perpendicular to the semipolar primary surface of the support base, and the opening defines the gain waveguide structure.

18. The group III nitride semiconductor laser device according to claim 1,
wherein the semiconductor region of the laser structure has a ridge structure, and
wherein the angle α1 and the angle β1 are defined on an axis located at a center of a width of an upper surface of the ridge structure, and the axis extends perpendicular to the semipolar primary surface of the support base.

19. A method for producing a group III nitride semiconductor laser device, comprising the steps of:
preparing a substrate made of a hexagonal group III nitride semiconductor and including a semipolar primary surface;
forming a substrate product including a laser structure and an electrode, the laser structure including the substrate and a semiconductor region formed on the semipolar primary surface; and
breaking the substrate product,
a c-axis of the group III nitride semiconductor of the substrate extending in a direction of a <0001> axis of the group III nitride semiconductor,
the direction of the <0001> axis being represented as a +c axis vector,
the step of breaking the substrate product comprising scribing a first surface of the substrate product and then pressing a second surface of the substrate product to form a laser bar and another substrate product, the laser bar having an angle α1 and an angle β1, the angle α1 being equal to or greater than 10 degrees but equal to or less than 25 degrees, and the angle β1 being equal to or greater than zero degrees but equal to or less than 5 degrees,
the scribing being executed in a direction intersecting with the +c axis vector,
the laser bar having a first surface and a second surface, the first surface being provided on opposite side of the second surface,
the laser bar having a first end facet and a second end facet, and each of the first end facet and the second end facet extending from the first surface to the second surface and being formed in the step of breaking the substrate product,
the first end facet and the second end facet forming a laser cavity of the group III nitride semiconductor laser device,
the first end facet and the second end facet intersecting with an m-n plane defined by an m-axis of the group III nitride semiconductor and a normal axis normal to the semipolar primary surface,
a first normal vector normal to the first end facet being defined at a first edge shared by the first end facet and the first surface, and the +c axis vector being inclined at the angle α1 with respect to the first normal vector within the m-n plane in a direction away from a [−1010] axis of the group III nitride semiconductor toward the c-axis,
a second normal vector normal to the first end facet being defined at a second edge shared by the first end facet and the second surface, and the +c axis vector being inclined at the angle β1 with respect to the second normal vector within the m-n plane in the direction from the [−1010] axis to the c-axis,
the semiconductor region including an active layer having a gallium nitride based semiconductor layer,
the semiconductor region being provided between the first surface and the substrate,
the c-axis of the group III nitride semiconductor of the substrate forming a nonzero angle ALPHA with the normal axis toward the direction of the [−1010] axis of the group III nitride semiconductor, the angle ALPHA being equal to or greater than 71 degrees but equal to or less than 79 degrees, and
the electrode being formed on the laser structure.

20. The method for producing a group III nitride semiconductor laser device according to claim 19,
wherein the scribing is executed using a laser scriber, and
wherein the scribing produces a scribe groove, the scribe groove is shorter than a line of intersection formed by the first surface with an a-n plane defined by the normal axis and an a-axis of the group III nitride semiconductor.

21. The method for producing a group III nitride semiconductor laser device according to claim 19,
wherein the scribing produces a scribe groove,
wherein the scribe groove extends from a front surface of the semiconductor region to the substrate, wherein the scribe groove has an opening in the front surface of the semiconductor region and a bottom portion in the substrate, and wherein a reference plane is defined by an end of the opening of the scribe groove and an end of the bottom portion of the scribe groove and extends in a direction of an a-n plane defined by the normal axis and an a-axis of the group III nitride semiconductor.

22. The method for producing a group III nitride semiconductor laser device according to claim 19, wherein, in the step of forming the substrate product, the substrate is processed by polishing to a thickness of 100 µm or less, and wherein the second surface is a processed surface formed by the processing or a plane including an electrode formed on the processed surface.

23. The method for producing a group III nitride semiconductor laser device according to claim 19, wherein the semipolar primary surface falls within a range of −4 degrees to +4 degrees from a {20-21} plane thereof.

24. The method for producing a group III nitride semiconductor laser device according to claim 19, wherein the substrate comprises one of GaN, AlGaN, AlN, InGaN and InAlGaN.

* * * * *